(12) United States Patent
Danitz et al.

(10) Patent No.: US 7,901,418 B2
(45) Date of Patent: Mar. 8, 2011

(54) CLAMP HAVING BENDABLE SHAFT

(75) Inventors: David J. Danitz, Cupertino, CA (US); David E. Hegeman, San Francisco, CA (US); Adam C. Gold, San Francisco, CA (US)

(73) Assignee: Vitalitec International, Inc., Plymouth, MA (US)

( * ) Notice: Subject to any disclaimer, the term of this patent is extended or adjusted under 35 U.S.C. 154(b) by 131 days.

(21) Appl. No.: 10/679,103

(22) Filed: Oct. 4, 2003

(65) Prior Publication Data

US 2004/0068280 A1 Apr. 8, 2004

Related U.S. Application Data

(63) Continuation of application No. 10/013,207, filed on Dec. 7, 2001, now Pat. No. 6,638,287, which is a continuation-in-part of application No. 09/847,135, filed on May 2, 2001, now Pat. No. 6,544,274.

(51) Int. Cl.
*A61B 17/08* (2006.01)

(52) U.S. Cl. ........................................................ 606/157

(58) Field of Classification Search .................. 606/157, 606/158, 205, 206, 151, 123, 124, 125, 139, 606/141, 50, 57; 604/523, 524, 525, 535; 600/123, 124, 101; 248/276.1
See application file for complete search history.

(56) References Cited

U.S. PATENT DOCUMENTS

| | | | |
|---|---|---|---|
| 2,677,901 A * | 5/1954 | Tilleman | 434/246 |
| 4,393,728 A * | 7/1983 | Larson et al. | 74/469 |
| 4,949,927 A * | 8/1990 | Madocks et al. | 248/276.1 |
| 5,318,528 A | 6/1994 | Heaven | |
| 5,395,367 A | 3/1995 | Wilk | |
| 5,411,514 A | 5/1995 | Fucci et al. | |
| 5,450,842 A | 9/1995 | Tovey | |
| 5,467,763 A | 11/1995 | McMahon et al. | |
| 5,511,564 A | 4/1996 | Wilk | |
| 5,514,076 A | 5/1996 | Ley | |
| 5,514,115 A | 5/1996 | Frantzen | |
| 5,558,665 A | 9/1996 | Kieturakis | |
| 5,593,416 A | 1/1997 | Donahue | |
| 5,626,607 A | 5/1997 | Malecki et al. | |
| 5,632,746 A | 5/1997 | Middleman | |
| 5,680,982 A | 10/1997 | Schulze et al. | |
| 5,752,969 A | 5/1998 | Cunci et al. | |
| 5,772,578 A | 6/1998 | Heimberger et al. | |
| 5,836,199 A * | 11/1998 | Loud | 72/466 |
| 5,851,208 A | 12/1998 | Trott | |
| 5,876,330 A | 3/1999 | Grabover et al. | |

(Continued)

FOREIGN PATENT DOCUMENTS

JP 404135554 11/1992

(Continued)

*Primary Examiner* — Anhtuan T Nguyen
*Assistant Examiner* — Tuan V Nguyen

(57) ABSTRACT

A clamp has a handle assembly, a gripping assembly having a pair of jaws that can be opened and closed to grip an element, and a shaft assembly. The shaft assembly has a flexible shaft having a proximal end that is operatively coupled to the handle assembly and a distal end that is operatively coupled to the gripping assembly. The shaft assembly also has a rigid element that can be placed in a first position where the rigid element supports the shaft in a manner where the shaft cannot be bent, and in a second position where the shaft can be bent.

6 Claims, 28 Drawing Sheets

U.S. PATENT DOCUMENTS

| | | | |
|---|---|---|---|
| 6,019,722 A * | 2/2000 | Spence et al. | 600/210 |
| 6,036,706 A | 3/2000 | Morejohn et al. | |
| 6,139,563 A * | 10/2000 | Cosgrove et al. | 606/205 |
| 6,146,394 A | 11/2000 | Morejohn et al. | |
| 6,156,047 A | 12/2000 | Spauling | |
| 6,544,274 B2 * | 4/2003 | Danitz et al. | 606/157 |
| 6,638,287 B2 * | 10/2003 | Danitz et al. | 606/157 |
| 6,676,676 B2 * | 1/2004 | Danitz et al. | 606/157 |
| 6,685,715 B2 * | 2/2004 | Danitz et al. | 606/157 |
| 6,730,020 B2 * | 5/2004 | Peng et al. | 600/201 |

FOREIGN PATENT DOCUMENTS

| | | |
|---|---|---|
| WO | WO 95/00197 | 1/1995 |
| WO | WO 98/24371 | 6/1998 |
| WO | WO 98/40020 | 9/1998 |
| WO | WO 99/42036 | 8/1999 |

\* cited by examiner

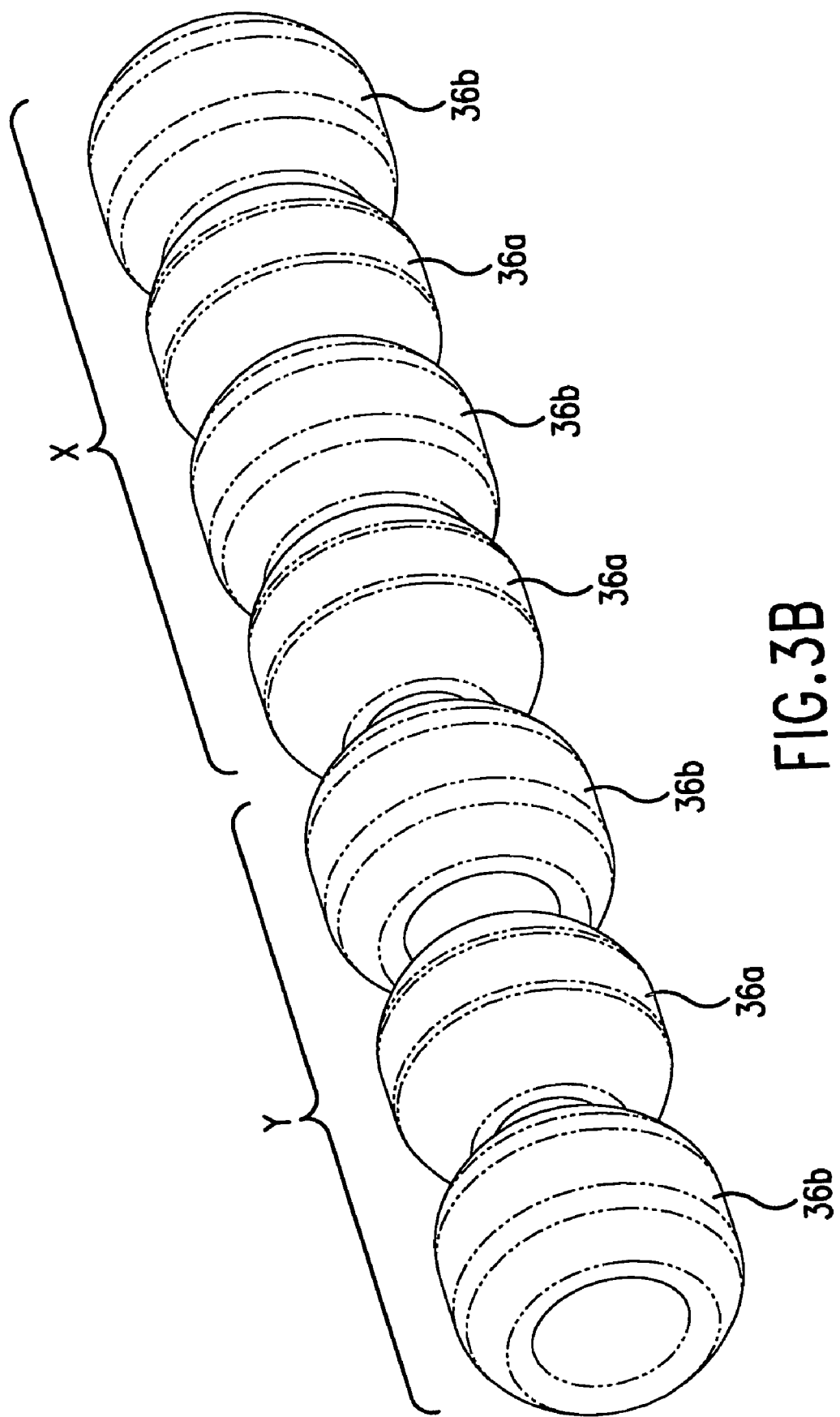

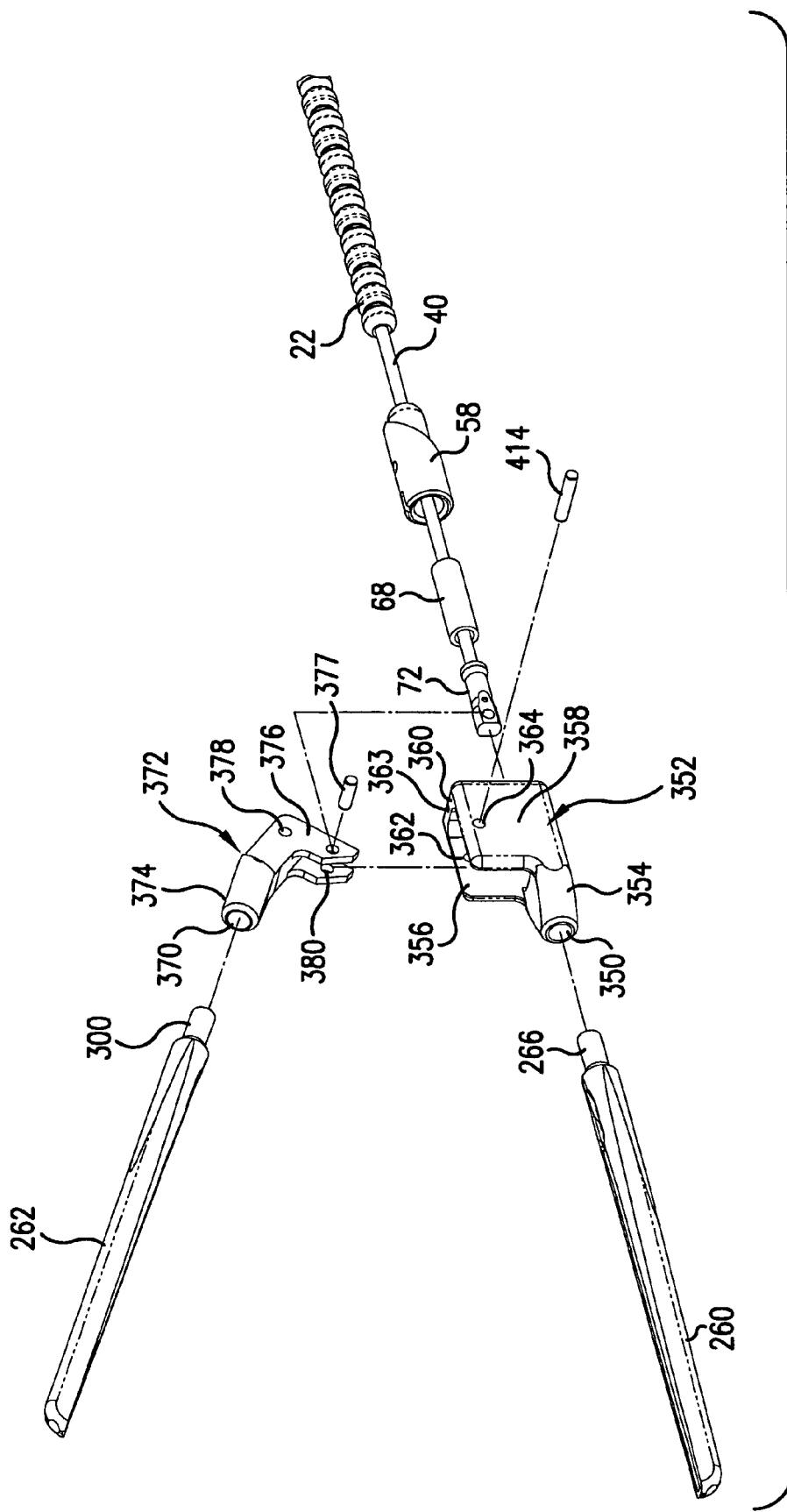

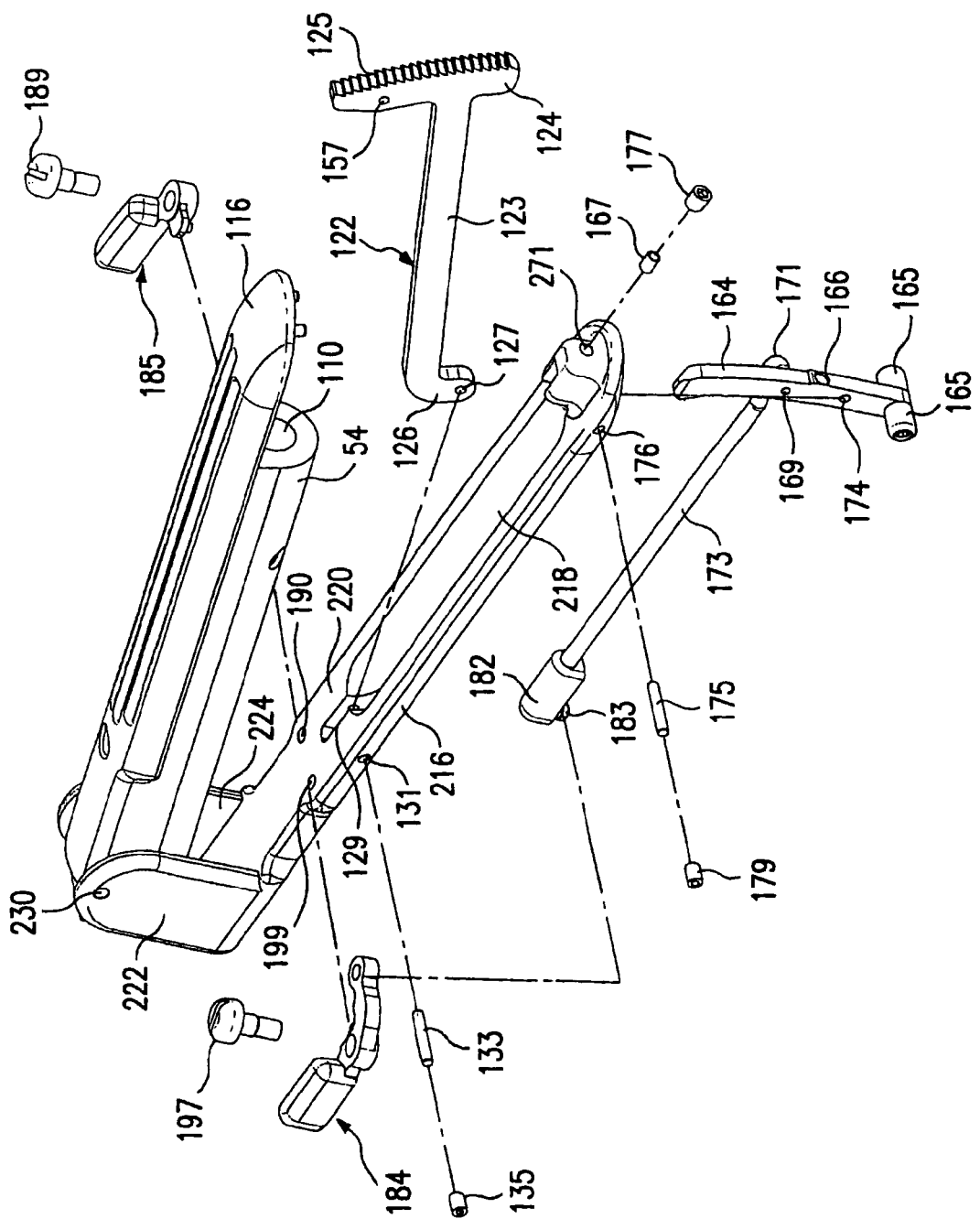

CLAMP HAVING BENDABLE SHAFT

RELATED CASES

This is a continuation of application Ser. No. 10/013,207 filed on Dec. 7, 2001 now U.S. Pat. No. 6,638,287, which is a continuation-in-part of application Ser. No. 09/847,135, filed May 2, 2001, now U.S. Pat. No. 6,544,274, whose disclosure is incorporated by this reference as though set forth fully herein.

BACKGROUND OF THE INVENTION

1. Field of the Invention

The present invention relates to medical devices, and in particular, to a clamping device that has a bendable shaft.

2. Description of the Prior Art

Clamping devices are typically used to occlude blood vessels during a surgical procedure. Conventional clamping devices are also known as clamps, and have a shaft that connects a pair of jaws with a handle at opposite ends thereof. The pair of jaws open and close about a pivot point in a motion that resembles that of a scissors. These conventional clamps are typically made from stainless steel and the shaft is therefore completely rigid. As a result, such conventional clamps are bulky and can interfere with the surgeon's access to the surgical site. To address this problem, elastic bands were sometimes used to hold the handles of the clamp away from the location of the surgical site.

With the increasing popularity of minimally invasive surgical procedures, access to the surgical site is reduced, thereby creating a need for smaller clamping devices, or clamping devices that can be moved away from the surgical site after the blood vessel has been clamped by the clamping device. As a result, the conventional clamps pose significant access problems to the surgeon when used during minimally invasive surgical procedures.

Thus, there remains a need for an improved clamping device that can be used to effectively clamp a blood vessel at a surgical site, while not interfering with the surgeon's access to the surgical site.

SUMMARY OF THE DISCLOSURE

It is an object of the present invention to provide a clamp that does not interfere with a surgeon's access to the surgical site during use.

It is another object of the present invention to provide a clamp that can effectively clamp a blood vessel at a surgical site.

It is yet another object of the present invention to provide a clamp whose handle can be moved away from the surgical site after the clamp has clamped the blood vessel.

It is yet another object of the present invention to provide a clamp that has a shaft which can be both completely rigid and completely flexible, with the rigid shaft being capable of withstanding axial loads, side loads, and moments applied to the jaws of the clamp.

It is yet another object of the present invention to provide a clamp that can be used in open and endoscopic surgeries.

It is yet another object of the present invention to provide a clamp that prevents rotation of the jaws when in use.

The objectives of the present invention are accomplished by providing a clamp having a handle assembly, a gripping assembly having a pair of jaws that can be opened and closed to grip an element, and a shaft assembly. The shaft assembly has a flexible shaft having a proximal end that is operatively coupled to the handle assembly and a distal end that is operatively coupled to the gripping assembly. The shaft assembly also has a rigid element that can be placed in a first position where the rigid element supports the shaft in a manner where the shaft cannot be bent, and in a second position where the shaft can be bent.

The clamp can be utilized in a surgical procedure by first introducing the jaws through a surgical site or a trocar, and then closing the jaws to grip a blood vessel, tissue or other anatomical structure. The rigid element can be withdrawn or otherwise removed so that the flexible shaft can be conveniently bent by the surgeon to a position or location so that the handle assembly does not interfere with access to the surgical site.

BRIEF DESCRIPTION OF THE DRAWINGS

FIG. 3B is a perspective view of a portion of the shaft of FIG. 3A.

FIG. 10 is an exploded perspective view of the gripping assembly of the clamp of FIG. 1.

FIG. 15 is an exploded perspective view of the handle assembly of the clamp of FIG. 1.

DETAILED DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. In certain instances, detailed descriptions of well-known devices and mechanisms are omitted so as to not obscure the description of the present invention with unnecessary detail.

The present invention provides a clamping device that has a flexible and bendable shaft that can be supported by a rigid element. When the clamping device is being held and controlled by the surgeon prior to clamping a blood vessel, tissue or other anatomical structure, the rigid element can be deployed to support the flexible shaft so that the entire clamping device is generally rigid. After the clamping device has been used to clamp a blood vessel, tissue or other anatomical structure, the rigid element can be withdrawn or otherwise removed so that the flexible shaft can be conveniently bent by the surgeon to a position or location so that the handle assembly does not interfere with access to the surgical site.

Figure 1:
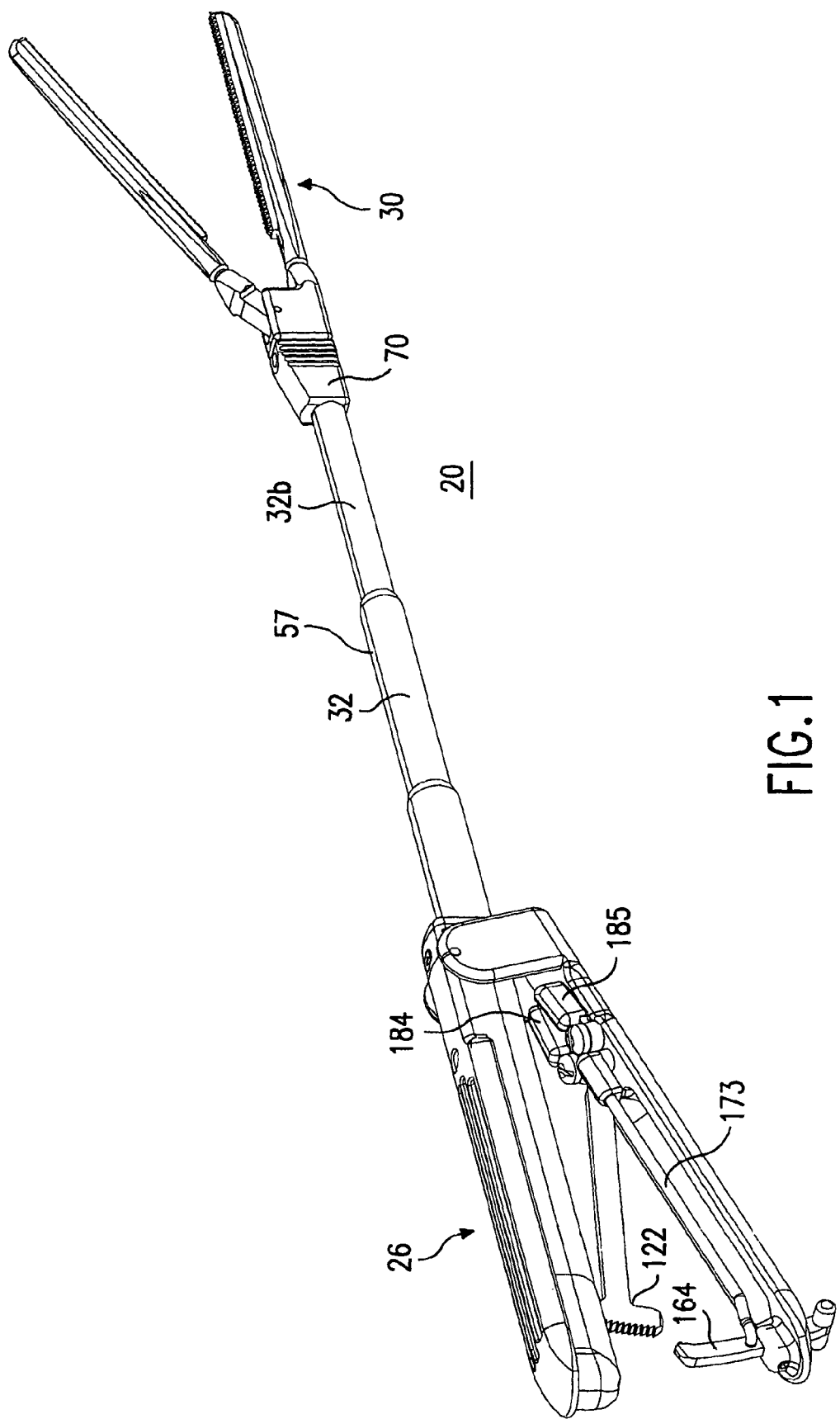
FIG. 1 is a perspective view of a clamp according to the present invention with the shaft completely covered by telescoping tubes.
Figure 2:
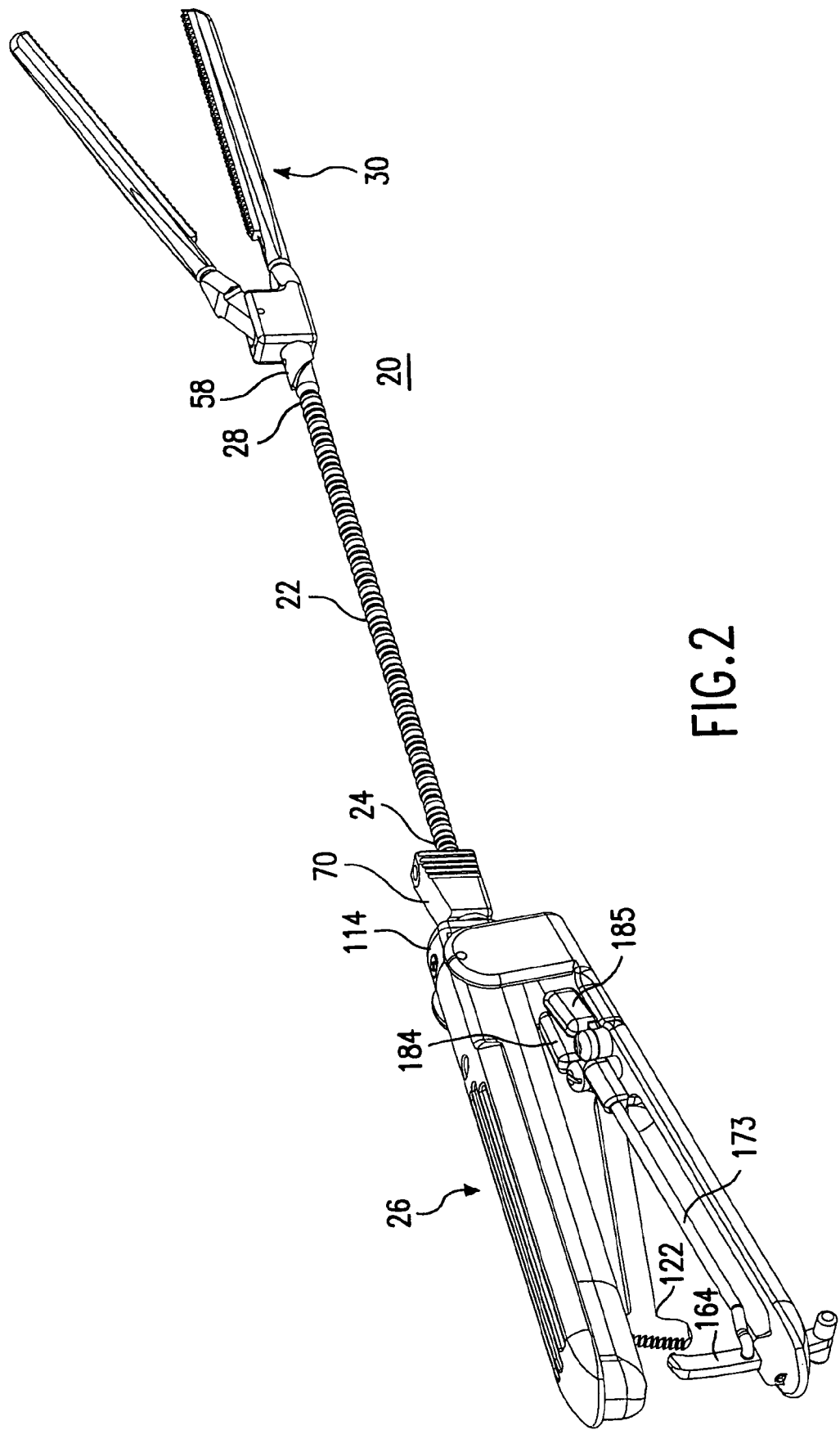
FIG. 2 is a perspective view of the clamp of FIG. 1 with the shaft not covered by telescoping tubes.

FIGS. 1 and 2 are perspective views illustrating the clamp 20 of the present invention. The clamp 20 has a shaft assembly having a flexible shaft 22 having a proximal end 24 that is operatively connected to a handle assembly 26, and a distal end 28 that is operatively connected to a gripping assembly 30. A plurality of telescoping tubes 32 can be withdrawn and stored in nested fashion inside the handle assembly 26 (see FIG. 2), or can be fully deployed to completely cover the shaft 22 (see FIG. 1).

Shaft Assembly and Telescoping Tubes

Referring now to FIGS. 2-5, the shaft 22 can be flexible to the point where it would be completely flexible (in other words, limp, flaccid, pliable, compliant and not stiff) when the shaft 22 is not supported by any other element, yet despite being completely flexible, is still capable of withstanding axial loads. In one embodiment that is best illustrated in FIGS. 3A and 3B, the shaft 22 can be made up of a plurality of two types of beads 36a and 36b that are alternated with respect to each other. Both types of beads 36a and 36b have a three-dimensional convex torus configuration, which is best shown in FIG. 3B. The first beads 36a have a smaller inner diameter than the second beads 36b. The first beads 36a have an outer diameter that is smaller than, equal to, or greater than, the outer diameter of the second beads 36b. Each second bead 36b rides (i.e., is supported) on the outer surface 37a of two adjacent first beads 36a, so that each second bead 36b is essentially in a raised position with respect to the first beads 36a. In particular, the convex circumferential portion 37b of each second bead 36b contacts or rides on the outer surface 37a of two adjacent first beads 36a. FIG. 3B illustrates four alternating beads 36a, 36b in a region X where all the beads 36a, 36b are shown connected to each other, and another three beads 36a, 36b in a region Y where the beads 36a, 36b are shown to be separated from each other solely for illustrative purposes. The beads 36a, 36b are preferably made of a material that is hard and stiff, with good wear properties. Non-limiting examples of such a material for the beads 36 include metal, plastics, composites and/or ceramics. Each bead 36a and 36b can have, in one embodiment, an inner diameter of about 0.03 to 0.20 and 0.05 to 0.22 inches, respectively, and an outer diameter of about 0.09 to 0.30 and 0.09 to 0.30 inches, respectively. Preferably, between a total of 10 to 100 beads 36a and 36b can be connected together to form the shaft 22.

Figure 3A:
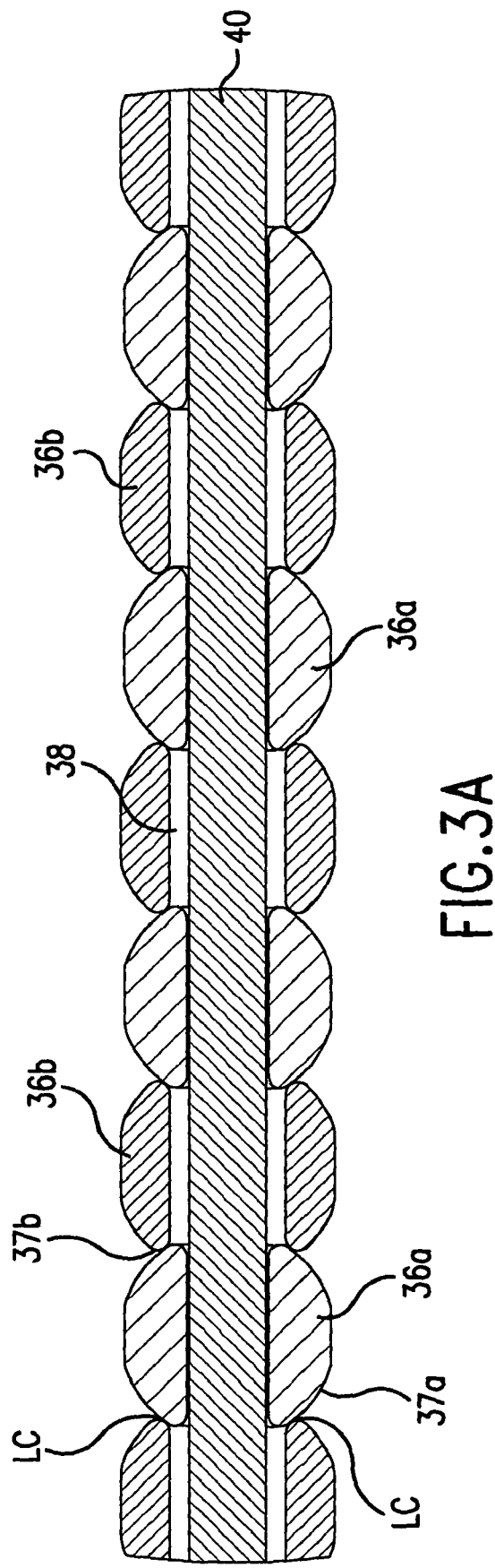
FIG. 3A is a cross-sectional view of a portion of the shaft of the clamp of FIG. 1.

As shown in FIG. 3A, each bead 36a, 36b can be provided with a through-hole or bore 38 so as to form a longitudinal bore through the shaft 22, with an internal wire cable 40 retained inside the bores 38. The beads 36 are lined up side-by-side in abutting fashion to form the shaft 22. The construction of a shaft 22 having alternating first and second beads 36a, 36b has exhibited improved flexibility even when the jaws 260, 262 of the gripping assembly 30 are clamped together. The contact between the adjacent beads 36a, 36b can be characterized as a line contact (as contrasted with conventional ball-and-socket joints which have surface contacts), in which one bead 36a contacts an adjacent bead 36a, 36b along a ring of points (e.g., LC in FIG. 3A). The construction of the beads 36a, 36b enables the line contact between adjacent beads 36a, 36b to exist at all times, even when the shaft 22 is bent. This line contact between the adjacent beads 36a, 36b also minimizes the friction between adjacent beads 36a, 36b when the shaft 22 is bent. As a result, the shaft 22 illustrated in FIGS. 3A and 3B will be more flexible when the jaws 260, 262 of the gripping assembly 30 are closed, so that when the surgeon moves the handle assembly 26 away from the surgical site, less torque or force is transmitted to the blood vessel by the gripping assembly 30, and trauma to the blood vessel can be minimized.

The cable 40 is always in tension, and is utilized to control the opening and closing of the jaws 260, 262 of the gripping assembly 30, as will be described in greater detail below. The cable 40 can be embodied in the form of any conventional cable that is used in clamping devices, and can be made, for example, from stainless steel or tungsten, among other examples.

Figure 4:
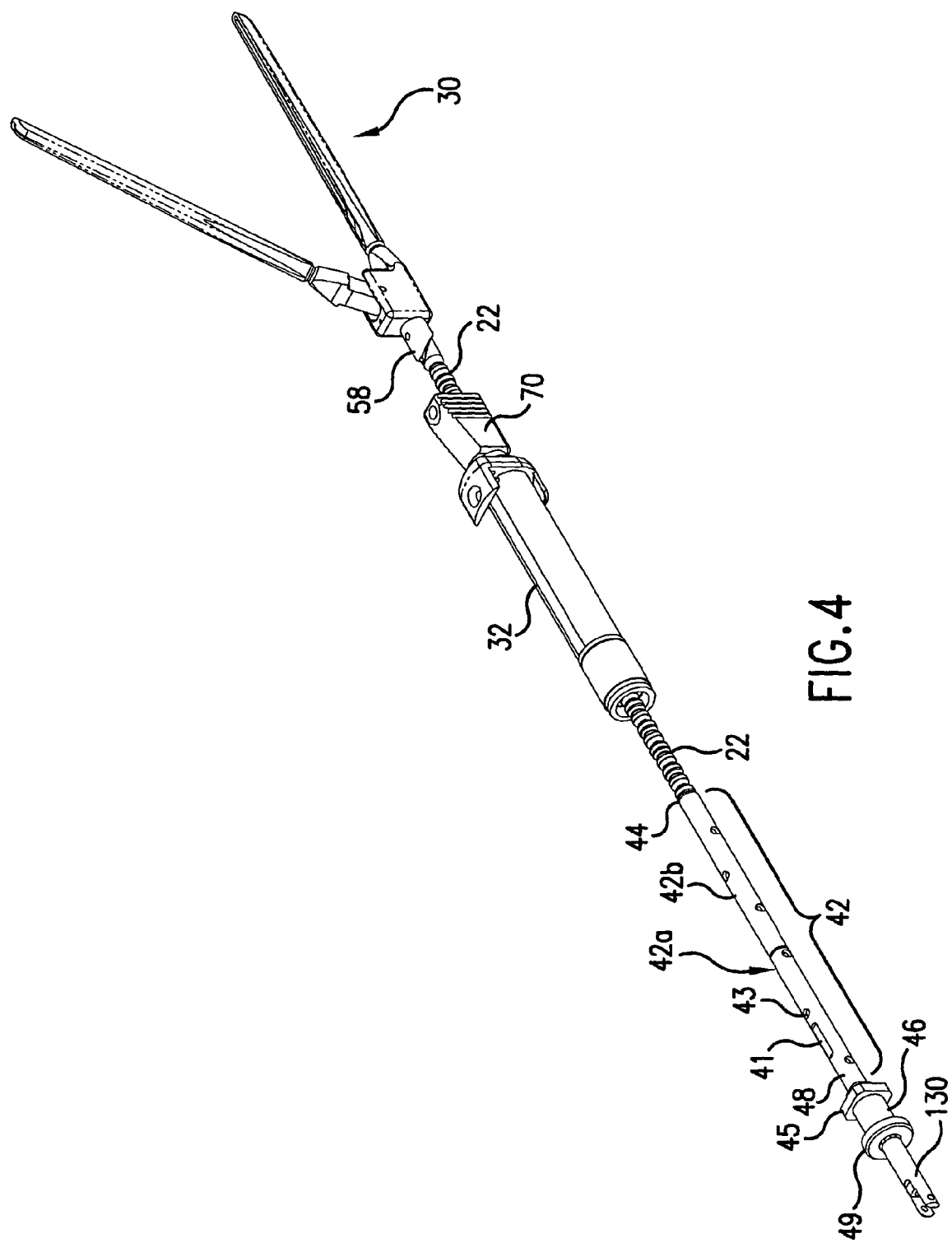
FIG. 4 is a perspective sectional view of the shaft assembly of the clamp of FIG. 1.
Figure 5:
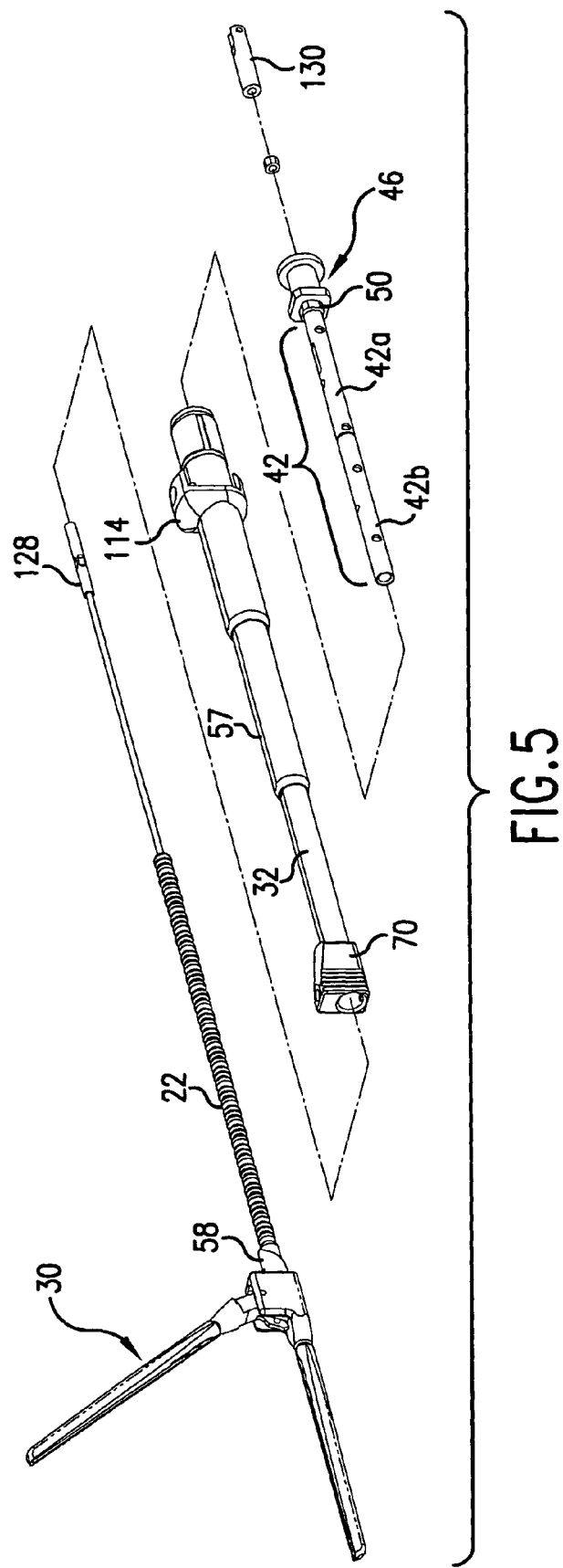
FIG. 5 is an exploded perspective view of the shaft assembly of the clamp of FIG. 1.
Figure 6A:
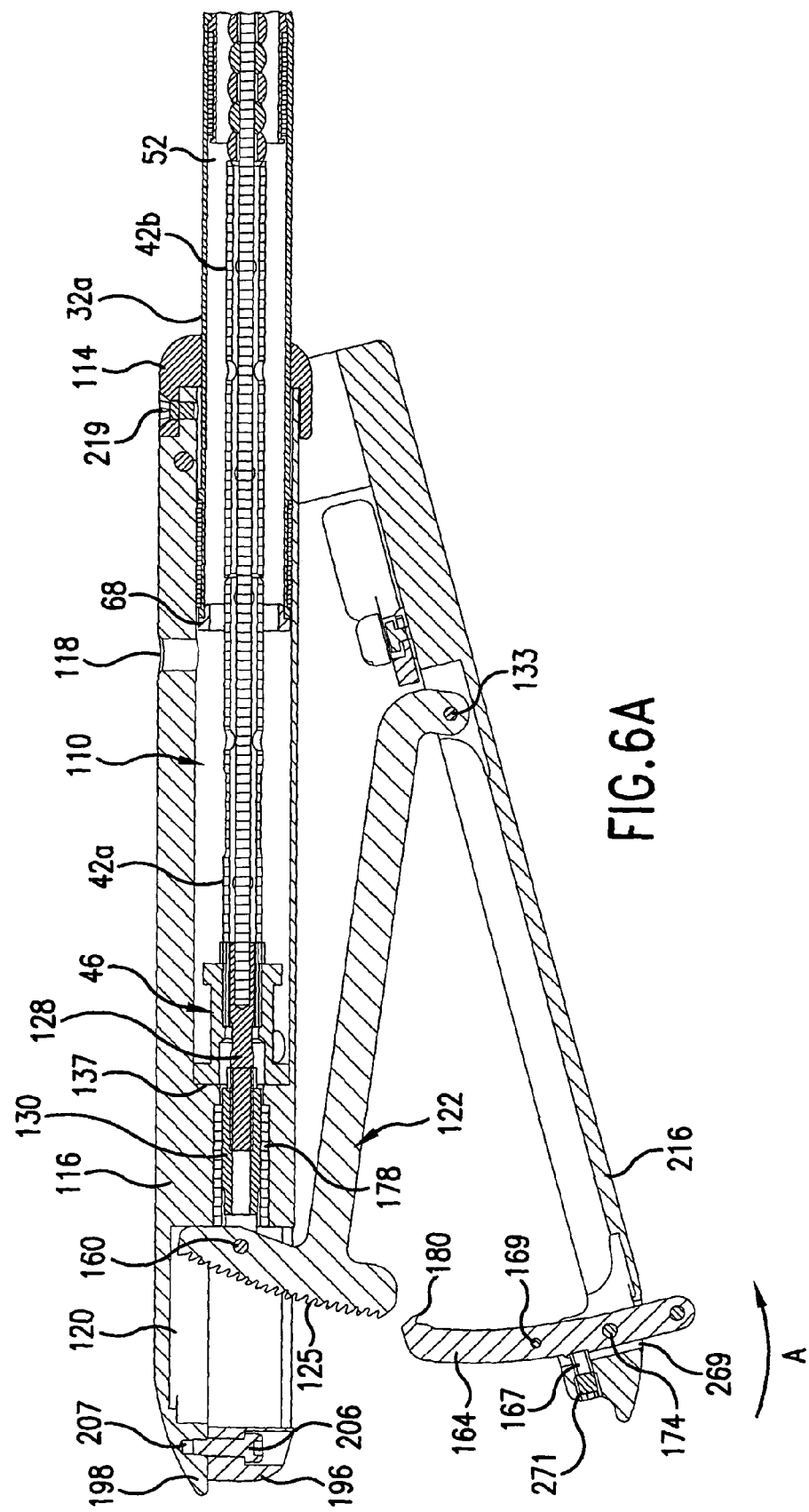
FIG. 6A is a cross-sectional view of the handle assembly of the clamp of FIG. 1 with the telescoping tubes deployed over the shaft.

The proximal end 24 of the shaft 22 abuts a distal end 44 of a proximal tube 42 that is secured inside the handle assembly 26, as shown in FIGS. 4 and 6A. The proximal tube 42 can be provided in one piece, or in a plurality of pieces (e.g., two separate pieces 42a, 42b as shown in FIGS. 4 and 5) for easier manufacturing, and can include holes 43 that allow for flushing of the cable 40 during cleaning. When provided in two or more pieces, each separate piece (e.g., 42a and 42b in FIG. 4) can have chamfered ends (not shown) that are adapted to mate or couple with the adjacent piece. In addition, one or more of the separate pieces 42a, 42b can have a flat region 41 that facilitates convenient gripping (e.g., by a wrench) during assembly of the clamp 20.

Figure 7:
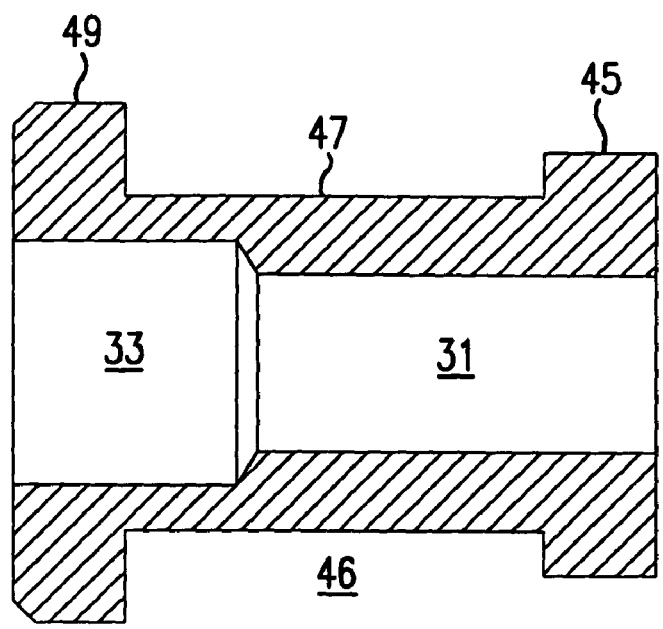
FIG. 7 is a cross-sectional view of the stop member of the clamp of FIG. 1.

The cable 40 extends through the interior of the proximal tube 42. A stop member 46 is threadably connected to the proximal end 48 of the tube 42. The stop member 46 acts as a stop member for the telescoping tubes 32, and in particular, the proximal-most telescoping tube 32a. Referring also to FIG. 7, the stop member 46 has a distal flange 45, a generally cylindrical shaft 47 and a proximal flange 49. A threaded bore 31 extends from an opening in the distal flange 45 to a central portion of the shaft 47, and a clearance hole 33 extends from an opening in the proximal flange 49 to the location where the threaded bore 31 terminates. The proximal-most end of the proximal tube 42 has external threads (not shown) which can be threadably engaged with the internal threads (not shown) inside the threaded bore 31 to couple the proximal tube 42 to the stop member 46. The proximal flange 49 acts as a stop member by abutting the proximal shoulder 137 of a bore 110 of the handle piece 116 (see FIG. 6A).

Referring to FIG. 5, a lock nut 50 can be threaded at the proximal-most end of the proximal tube 42 to secure the threaded connection between the proximal tube 42 and the stop member 46. The length of the threaded connection between the tube 42 and the stop member 46 can be adjusted by the manufacturer of the clamp 20 during the assembly of the handle assembly, simply by rotating one of the stop member 46 or the proximal tube 42 with respect to the other about the threaded connection. Adjusting the length of the threaded connection between the tube 42 and the stop member 46 allows the length of the shaft 22 to be adjusted, which in turn allows for (i) tensioning of the cable 40, and (ii) adjustment the maximum opening angle of the jaws 260, 262 of the gripping assembly 30. In this regard, the manufacturer can increase or decrease the length of the threaded connection between the tube 42 and the stop member 46 by turning stop member 46 or tube 42 with respect to each other, and then tightening the lock nut 50 to prevent the threaded connection from coming loose. When the length of the threaded connection (between the stop member 46 and the tube 42) is decreased, the stop member 46 and the tube 42 are moved away from each other, thereby increasing the length of the shaft 22. By increasing the length of the shaft 22, the length of the cable 40 that protrudes from each end of the shaft 22 is decreased. This effectively decreases the length of the cable 40 relative to the shaft 22, which increases the maximum tension in the cable 40 and decreases the maximum opening angle of the jaws of the gripping assembly 30. Similarly, by increasing the length of the threaded connection, the stop member 46 and the tube 42 are moved towards each other, thereby decreasing the length of the shaft 22. This effectively increases the length of the cable 40 relative to the shaft 22, which decreases the maximum tension in the cable 40 and increases the maximum opening angle of the jaws of the gripping assembly 30.

A plurality of telescoping tubes 32 can be used to provide rigidity to the beaded shaft 22. Each telescoping tube 32 has an inner bore 52. Any number of telescoping tubes 32 can be provided, and according to one embodiment of the present invention, one to five telescoping tubes 32 are provided. Each telescoping tube 32 can have any desired cross-section (e.g., circular, square, rectangular or elliptical, among others), and is preferably made from a substantially rigid material, such as plastic, aluminium, titanium and stainless steel, among others. The proximal-most telescoping tube 32a has the largest diameter and largest inner bore 52, while the diameters and sizes of the inner bores 52 of the intermediate telescoping tubes 32 become progressively smaller until the distal-most telescoping tube 32b, which has the smallest diameter and smallest inner bore 52. This configuration allows the plurality of telescoping tubes 32 to be nested within each other and stored inside the handle assembly 26.

Figure 28:
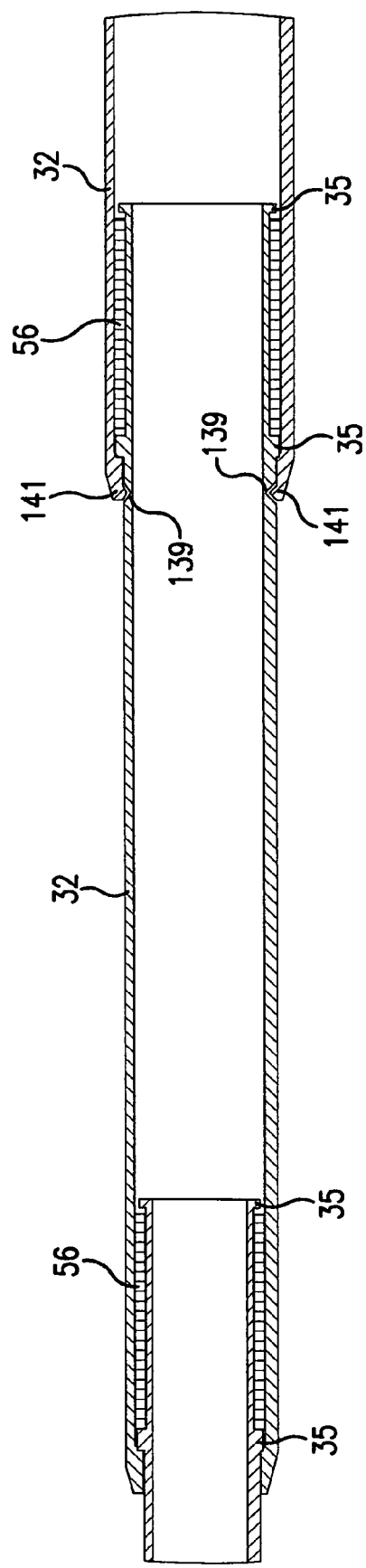
FIG. 28 is a cross-sectional view illustrating the nesting of adjacent telescoping tubes of the clamp of FIG. 1.

The telescoping tubes 32 can be locked or secured in their fully deployed configuration that is shown in FIG. 1. To accomplish this, the outer surface of each tube 32 can be provided with one or more dimples 139 that are positioned to engage corresponding locking tabs 141 that are provided at the distal end of each of the tubes 32. See FIG. 28. The distal-most tube 32b does not need to have a tab 141. Each tab 141 can be slid back and forth along the outer surface of the smaller adjacent tube 32 as the two adjacent tubes 32 reciprocate with respect to each other, and can be clicked into the corresponding dimple 139 during this sliding motion. The tab 141 can be compliant enough so that a sufficiently large axial force will disengage the tab 141 from the corresponding dimple 139 for further sliding motion.

Figure 6B:
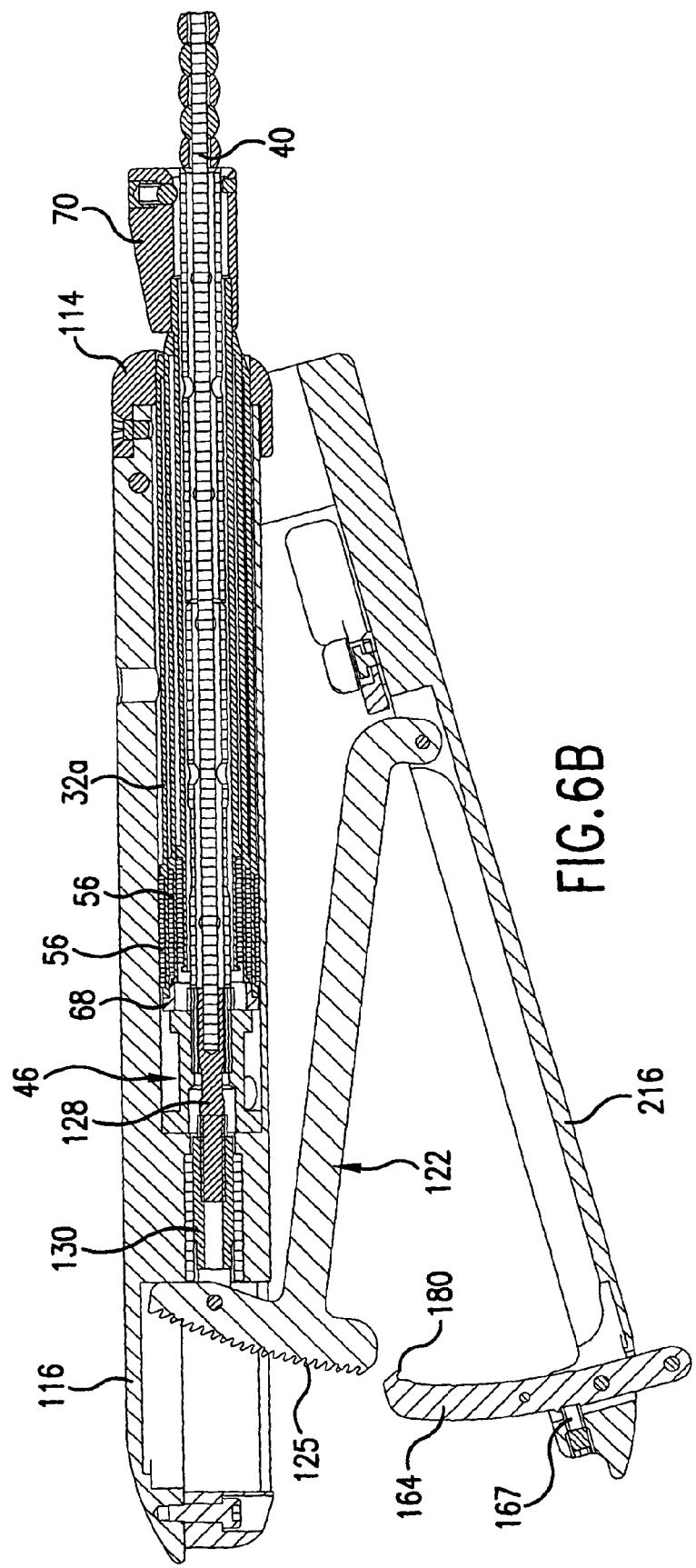
FIG. 6B is a cross-sectional view of the handle assembly of the clamp of FIG. 1 with the telescoping tubes retained inside the handle assembly.
Figure 8:
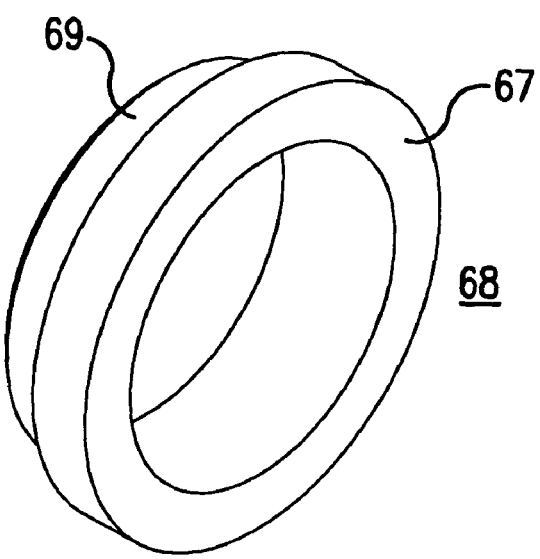
FIG. 8 is an isolated perspective view of the proximal tube bushing of the clamp of FIG. 1.

Each telescoping tube 32 also has an internal bushing 56 (see FIGS. 6B and 28) that is provided on the outer surface at the proximal end of each telescoping tube 32. Each bushing 56 is cylindrical in nature and is retained for sliding movement between the outer surface of the smaller tube 32 and the inner surface of the adjacent larger tube 32. The proximal end of each telescoping tube 32 is provided with a pair of bosses 35 that capture (axially) the bushing 56 that couples an adjacent telescoping tube 32 when the telescoping tubes 32 are withdrawn. Referring to FIGS. 6A, 6B and 8, a proximal stop member 68 is attached (e.g., by glue, screws, brazing or welding) to the proximal-most telescoping tube 32a to act as a stop member for the adjacent (and smaller-diameter) telescoping tube 32. The proximal stop member 68 has a generally circular proximal surface 67 that abuts against the distal flange 45 of the stop member 46 when all the telescoping tubes 32 are withdrawn and retained inside the handle assembly 26. A narrow-diameter flange 69 extends from the distal side of the proximal stop member 68 and is adapted to be pressed into the inner diameter at the proximal end of the proximal-most telescoping tube 32a. The outer diameter of the proximal stop member 68 is sized to allow the proximal stop member 68 to slide inside a bore 110 of the handle piece 116 (see FIGS. 6A and 6B) that is described in greater detail hereinbelow.

The bushings 56 function to promote smooth sliding of the telescoping tubes 32 within each other, and to promote stiffness to the region of the shaft 22 when the shaft 22 is completely covered by the telescoping tubes 32. With respect to the promotion of the smooth sliding of the telescoping tubes 32 within each other, the bushings 56 can be made of a harder or softer stainless steel than the telescoping tubes 32, or can be made from plastic. The smooth sliding of the telescoping tubes 32 will be achieved by the smooth surface finish of the bushings 56 and the telescoping tubes 32. If the bushings 56 are made of plastic, the smooth sliding will also be achieved by the low coefficient of friction between the telescoping tubes 32 and the bushings 56. With respect to the promotion of stiffness, the overlap between the ends of adjacent telescoping tubes 32 functions to counter any side-load or moment applied to the jaws 260, 262 of the gripping assembly 30.

Figure 27:
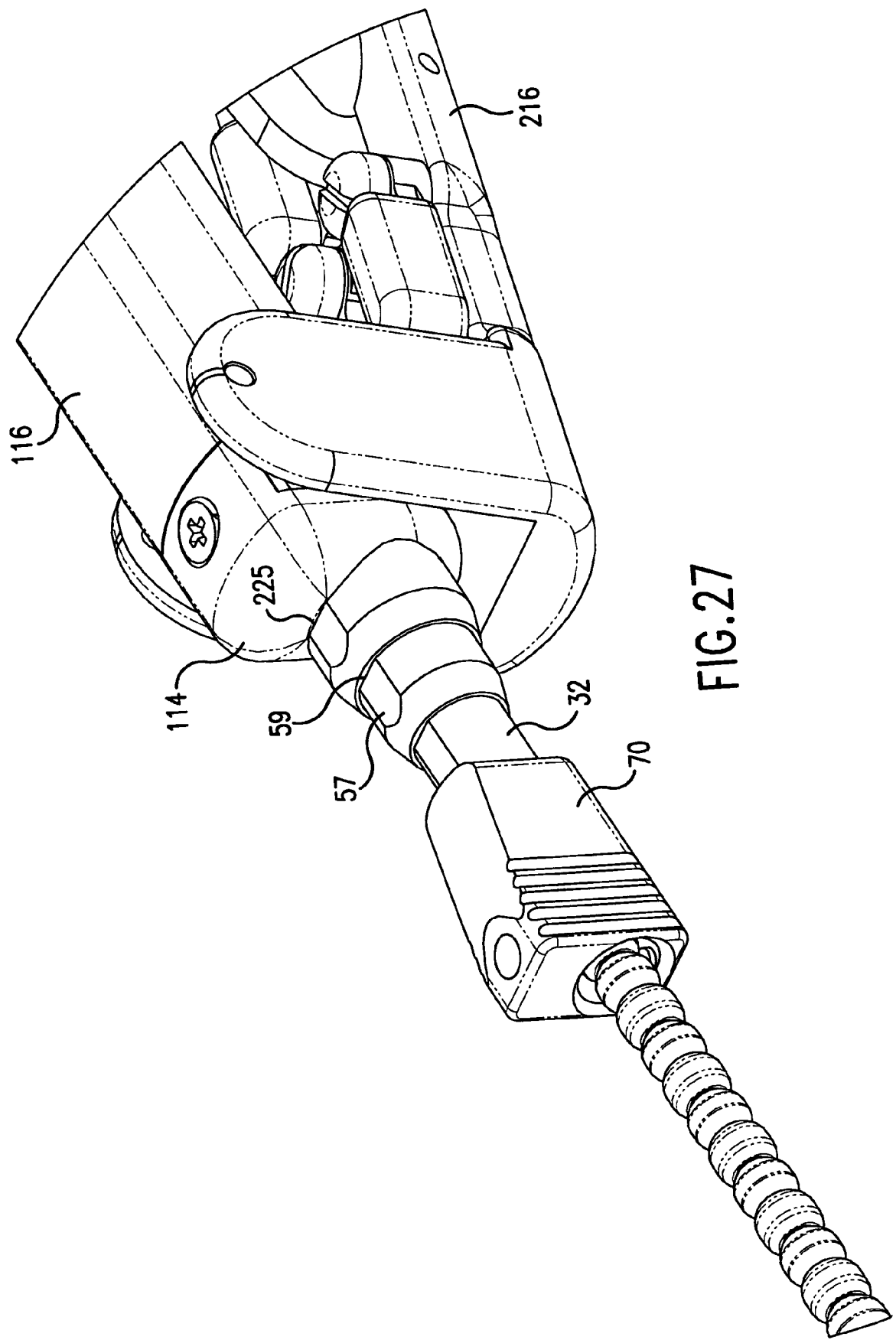
FIG. 27 is an enlarged sectional perspective view of the proximal part of the shaft of the clamp of FIG. 1.

If the cross-section of the telescoping tubes 32 is round, then a flat or curved (e.g., concave) surface (e.g., see 57 in FIGS. 1, 5 and 27) can be machined or otherwise provided on the outer surface of each telescoping tube 32, and another corresponding flat or curved surface 59 may be machined in the inner surface of the bore 52 of each telescoping tube 32 to guide the corresponding surface 57 of the adjacent telescoping tube 32. This mating correspondence between the surfaces 57 and 59 will prevent the telescoping tubes 32 from rotating with respect to each other when the shaft 22 is torqued during use of the clamp 20. The surfaces 57 and 59 function like keyways so that the surface 59 on the inner surface of the bore 52 can ride along the surface 57 on the outer surface of the adjacent and smaller telescoping tube 32.

The Handle Assembly

The handle assembly 26 is best illustrated in FIGS. 1, 2, 4, 5, 6A, 6B and 15. The handle assembly 26 has a pivoting elongated handle piece 216, and a stationary handle piece 116 that includes a cylindrical tube 54 having a bore 110 extending therethrough. A ratchet assembly is provided between the handle pieces 116, 216 for locking the jaws 260, 262 of the gripping assembly 30 at varying degrees of clamping force.

Figure 16:
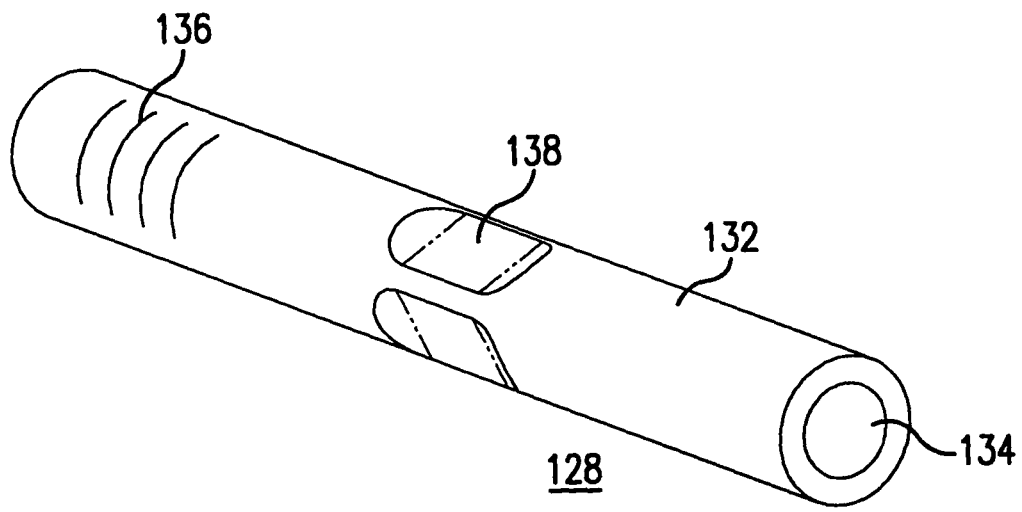
FIG. 16 is a perspective view of the cable holder of the handle assembly of the clamp of FIG. 1.

The handle assembly 26 houses a cable terminator assembly that comprises a cable holder 128 and an adjuster piece 130. FIG. 16 provides an isolated view of the cable holder 128, which has a generally cylindrical body 132 having a bore 134 that extends from its distal end to a location inside the body 132 between the distal and proximal ends of the body 132. The proximal-most end of the cable 40 is secured (e.g., by brazing or crimping) inside the bore 134. External threads 136 can be provided on the outer surface of the cable holder 128 adjacent its closed proximal end. One or more flat regions 138 can be provided on the outer surface of the cable holder 128 to facilitate convenient gripping (e.g., by a wrench) when the cable holder 128 is being threadably connected to the adjuster piece 130.

Figure 17:
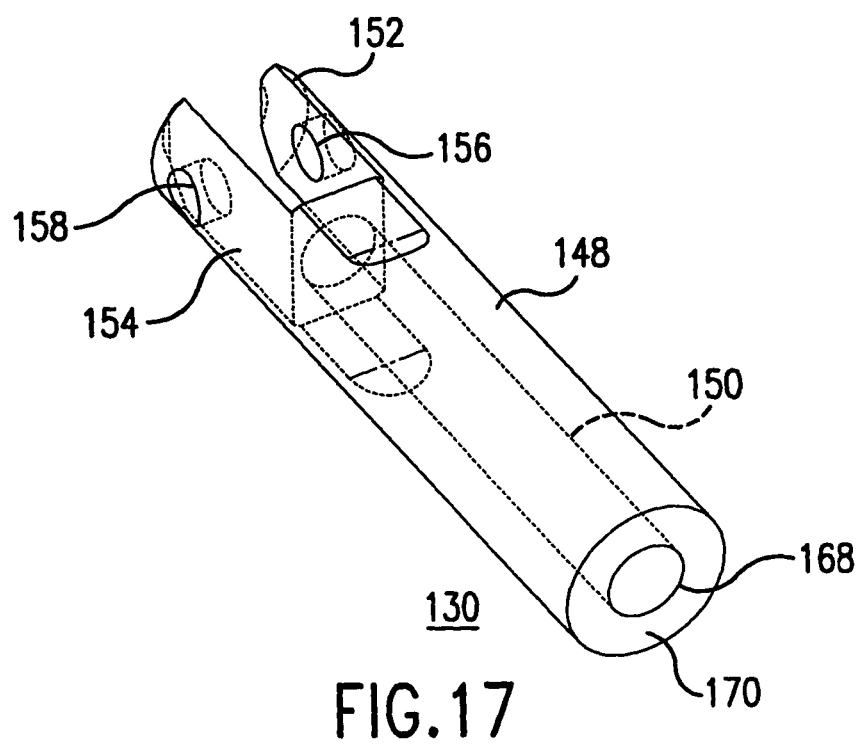
FIG. 17 is a perspective view of the adjuster piece of the handle assembly of the clamp of FIG. 1.

FIG. 17 provides an isolated view of the adjuster piece 130, which has a generally cylindrical body 148 having a threaded bore 150 extending therethrough. Two opposing walls 152 and 154 extend from the proximal end of the cylindrical body 148 to define an internal space therebetween. Each wall 152 and 154 has an opening 156 and 158, respectively, that are aligned with each other and through which a pin 160 can be extended (see FIG. 6A). The internal space between the walls 152, 154 is adapted to receive (in a pivoting connection) the transverse piece 124 of a ratchet rack 122, with the pin 160 inserted through the openings 156, 158, and an aligned opening 157 in the transverse piece 124 (see FIG. 15) to create a pivoting connection between the transverse piece 124 and the adjuster piece 130. The proximal end of the cable holder 128 is inserted into the bore 150 of the adjuster piece 130 via an opening 168 in the distal face 170 of the adjuster piece 130. The external threads 136 on the cable holder 128 threadably engage the internal threads in the bore 150 to secure the cable holder 128 to the adjuster piece 130.

In addition to adjusting or calibrating the maximum tension in the cable 40 and the maximum opening angle of the jaws 260, 262 of the gripping assembly 30 by adjusting the length of the shaft 22 (as described above), the maximum tension in the cable 40 and the maximum opening angle of the jaws 260, 262 of the gripping assembly 30 can also be adjusted or calibrated by changing the length of the cable 40 directly. The maximum tension of the cable 40 and the maximum opening angle of the jaws 260, 262 of the gripping assembly 30 can be adjusted or calibrated by turning the adjuster piece 130 when the pin 160 does not couple the adjuster piece 130 to the transverse piece 124. For example, when the pin 160 is removed from the openings 156, 158 and 157, the transverse piece 124 can be separated from the adjuster piece 130. This can only be done by the manufacturer. By rotating the adjuster piece 130, the threads 136 on the cable holder 128 translate in the threaded bore 150 to either increase or decrease the length of the cable 40 (depending on the direction of rotation). By decreasing the length of the cable 40, the jaws 260, 262 of the gripping assembly 30 close slightly, and the maximum force that the cable 40 can transmit to the jaws 260, 262 is increased. By increasing the length of the cable 40, the jaws 260, 262 open slightly, and the maximum force that the cable 40 can transmit to the jaws 260, 262 is decreased.

Referring to FIG. 6A, the handle assembly 26 further houses a plastic bushing 178 that is cylindrical in configuration and has a hollow bore through which the adjuster piece 130 can slide in a reciprocal manner. The plastic bushing 178 functions to allow the adjuster piece 130 to slide smoothly therethrough, and also prevents wear and tear between the adjuster piece 130 and the handle piece 116.

Figure 18:
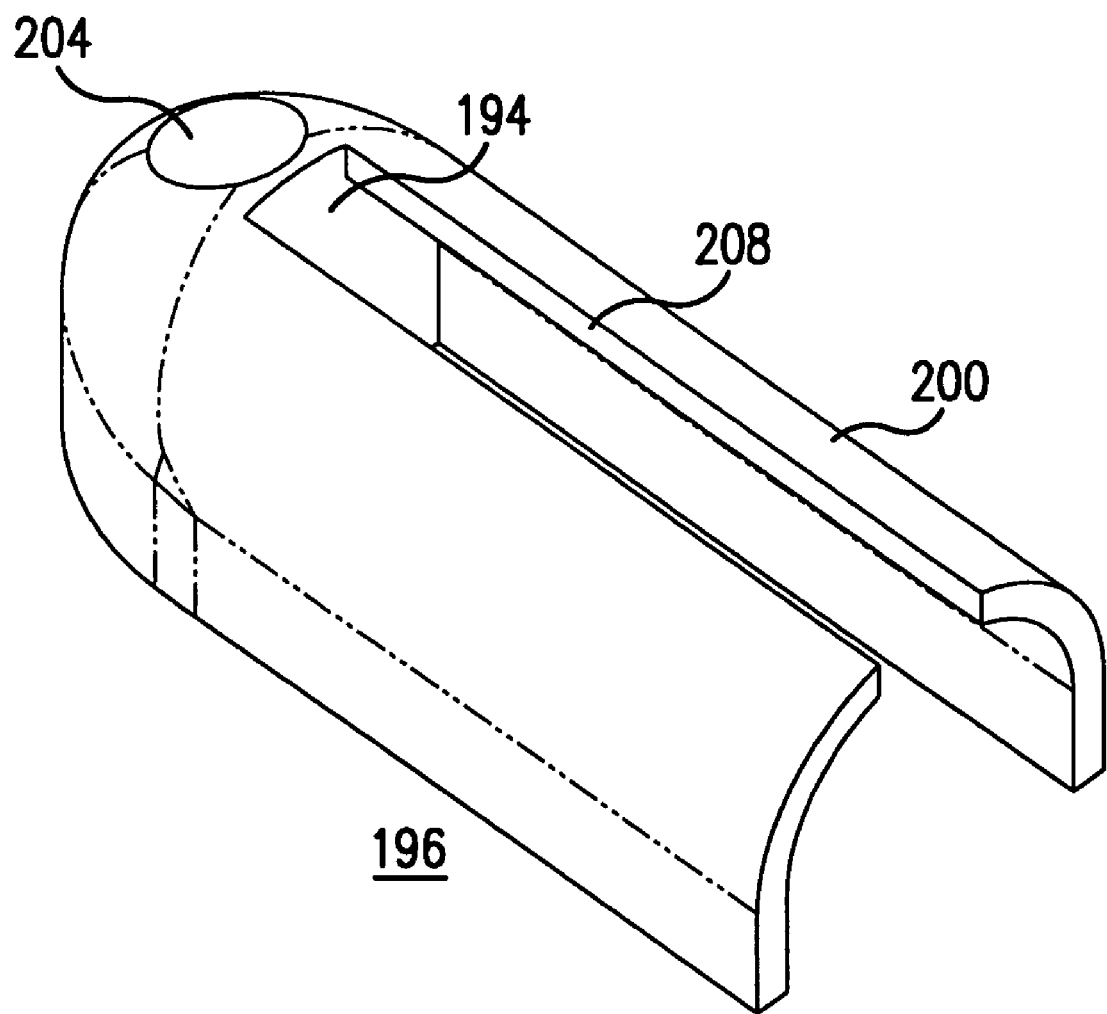
FIG. 18 is a perspective view of the end housing of the handle assembly of the clamp of FIG. 1.

As shown in FIG. 6A, an end housing 196 is attached to the proximal end 198 of the handle piece 116. FIG. 18 provides an isolated view of the end housing 196, which has a solid section 194 and a groove section 200. A longitudinal slit 208 is provided along the bottom of the groove section 200 to allow the transverse piece 124 to reciprocate therewithin. The solid section 194 of the end housing 196 has one through-hole 204 through which a threaded screw 206 can be inserted to connect the end housing 196 to a corresponding threaded opening 207 at the proximal end 198 of the handle piece 116.

Figure 19:
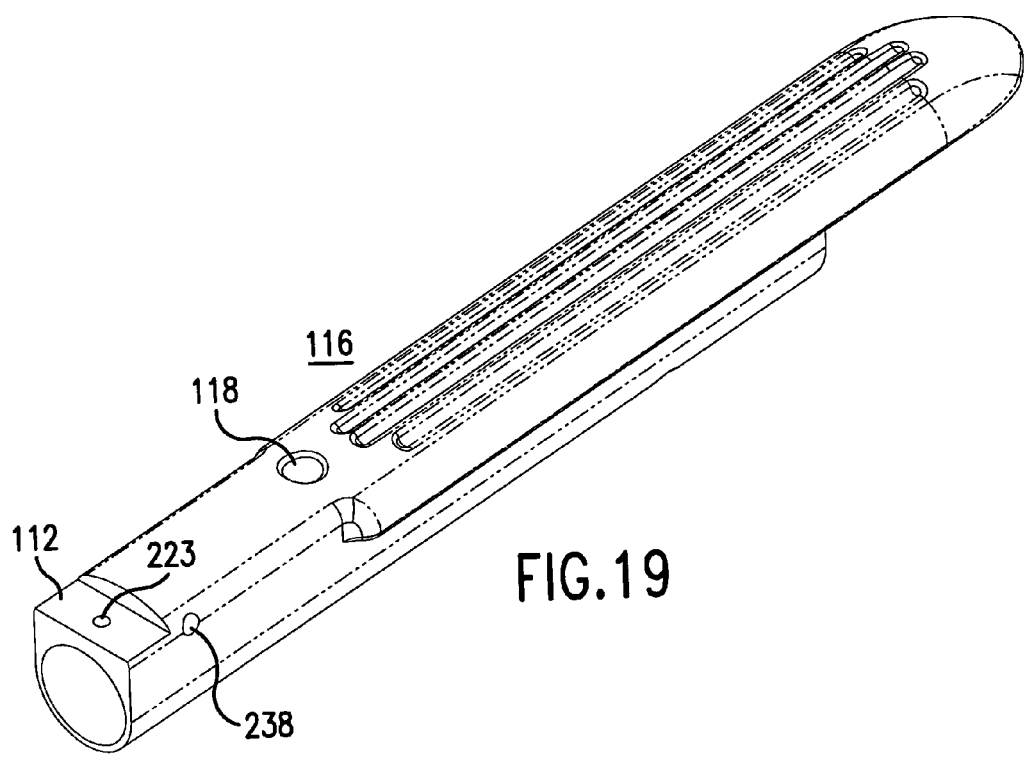
FIG. 19 is a perspective view of one handle piece of the handle assembly of the clamp of FIG. 1.

FIG. 19 provides an isolated top perspective view of the handle piece 116. Referring to FIGS. 6A and 19, the handle piece 116 has a cut-away section 112 at its distal end for receiving the upper boss 213 of a handle end piece 114. A flush port 118 is provided on the handle piece 116 to allow for cleaning of the components housed inside the handle piece 116 and its bore 110. A slot 120 is provided on the underside of the handle piece 116 adjacent its proximal end to provide clearance for the transverse piece 124 of the ratchet rack 122.

Figure 20:
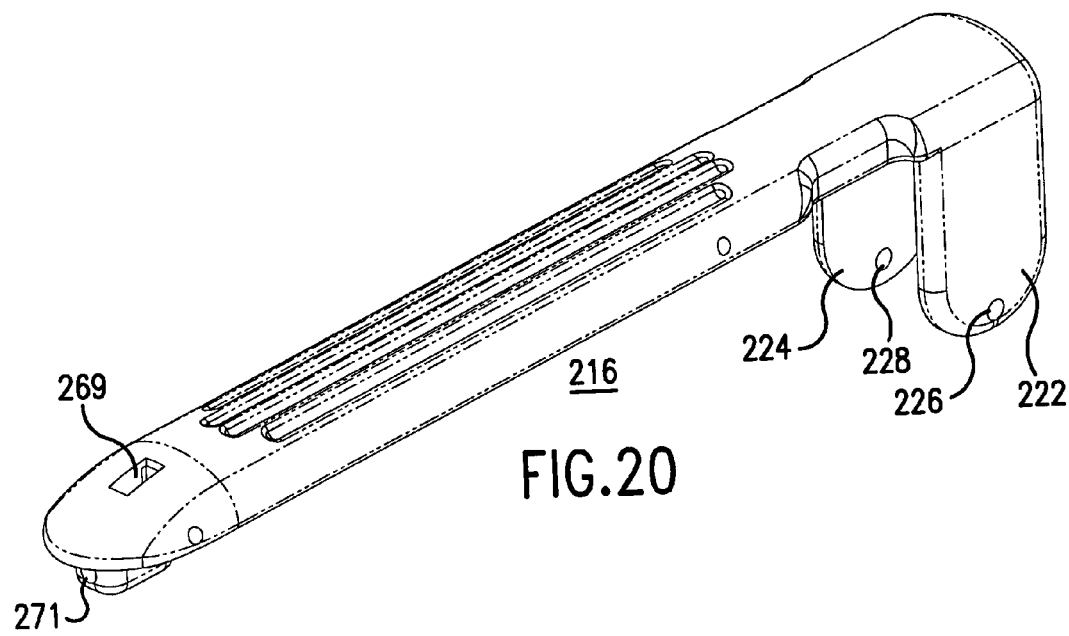
FIG. 20 is a perspective view of another handle piece of the handle assembly of the clamp of FIG. 1.

FIG. 20 provides an isolated bottom perspective view of the handle piece 216. Referring to FIGS. 6A, 15 and 20, the handle piece 216 has a longitudinal channel 218 provided on its inner surface 220. Two opposing walls 222 and 224 extend from the distal end of the handle piece 216 to define an internal space therebetween. Each wall 222 and 224 has a first opening 226 and 228, respectively, that are aligned with each other and through which a first pin 230 can be extended. The internal space between the walls 222, 224 is adapted to receive the body of the handle piece 116, with the first pin 230 inserted through the first openings 226, 228, and an aligned opening 238 (see FIG. 19) in the handle piece 116 to create a pivoting connection between the handle pieces 116 and 216. The longitudinal channel 218 is adapted to receive the ratchet rack 122 when the handle pieces 116 and 216 are gripped together (i.e., closed).

Referring to FIGS. 6A and 15, the ratchet assembly includes a ratchet 164 and a ratchet rack 122 that are removably engageable to allow the handle pieces 116, 216 to be closed, or to be locked at a desired angle with respect to each other. The ratchet rack 122 has a transmission link 123 and a transverse piece 124 at the proximal end of the link 123. The transverse piece 124 has a plurality of teeth 125 provided on its proximal-facing surface. A hooked end 126 extends from the distal end of the link 123, and has a hole 127. The hooked end 126 is retained in a narrowed channel 129 that extends from the distal end of the longitudinal channel 218 in the handle piece 216. An opening 131 extends through the side wall of the handle piece 216 from the exterior into the narrowed channel 129, and a pin 133 extends through the opening 131 and the hole 127 in the ratchet rack 122 to provide a pivoting connection between the ratchet rack 122 and the handle piece 216. A set screw 135 can be provided to secure the pin 133 in the openings 127 and 131.

The ratchet 164 essentially comprises a vertical piece that has two small and rounded handles 165 provided on either side at its bottom. The handles 165 can be used by the surgeon to disengage the ratchet 164 from the ratchet rack 122. The ratchet 164 has a first counterbore 166 in its proximal face which is adapted to receive a spring 167. The ratchet 164 also has a second counterbore 169 extending through its side wall for receiving a hooked proximal end 171 of a transmission rod 173. The ratchet 164 also has an opening 174 extending through its side wall for receiving a dowel pin 175 that also extends through an opening 176 in the side wall of the handle piece 216. Set screws 177 and 179 can be provided for securing the spring 167 and the dowel pin 175, respectively. In addition, a ratchet tooth 180 is provided at the upper end of the ratchet 164 in the distal-facing direction, and is adapted to engage one of the teeth 125 on the ratchet rack 122. The ratchet 164 extends vertically through a hole 269 in the handle piece 216, and the spring 167 extends into another hole 271 in the handle piece 216 that is transverse to the hole 269. In other words, the paths of the holes 269 and 271 are perpendicular to each other. The spring 167 naturally biases the upper end of the ratchet 164 towards the ratchet rack 122 about the pivot point defined by the dowel pin 175, so that the tooth 180 can be made to engage a selected tooth 125.

The transmission rod 173 has a hooked proximal end 171 that is pivotably coupled to the ratchet 164 at the opening 169. The distal end of the rod 173 is coupled, such as by a threaded connection, to a threaded bore (not shown) in a gimble 182. By threading the rod 173 further in or out of the threaded bore in the gimble 182, the angle of the ratchet 164 with respect to the handle piece 216 can be fine-tuned for optimal engagement between the teeth 180 and 125. The gimble 182 has a boss 183 that extends from the bottom surface of the gimble 182.

Referring to FIGS. 15 and 24-26, the ratchet assembly further includes a first ratchet release button 184 and a second ratchet release button 185 that operate in conjunction with the gimble 182 and the transmission rod 173 to release the engagement of the ratchet 164 with the ratchet rack 122.

Figure 21:
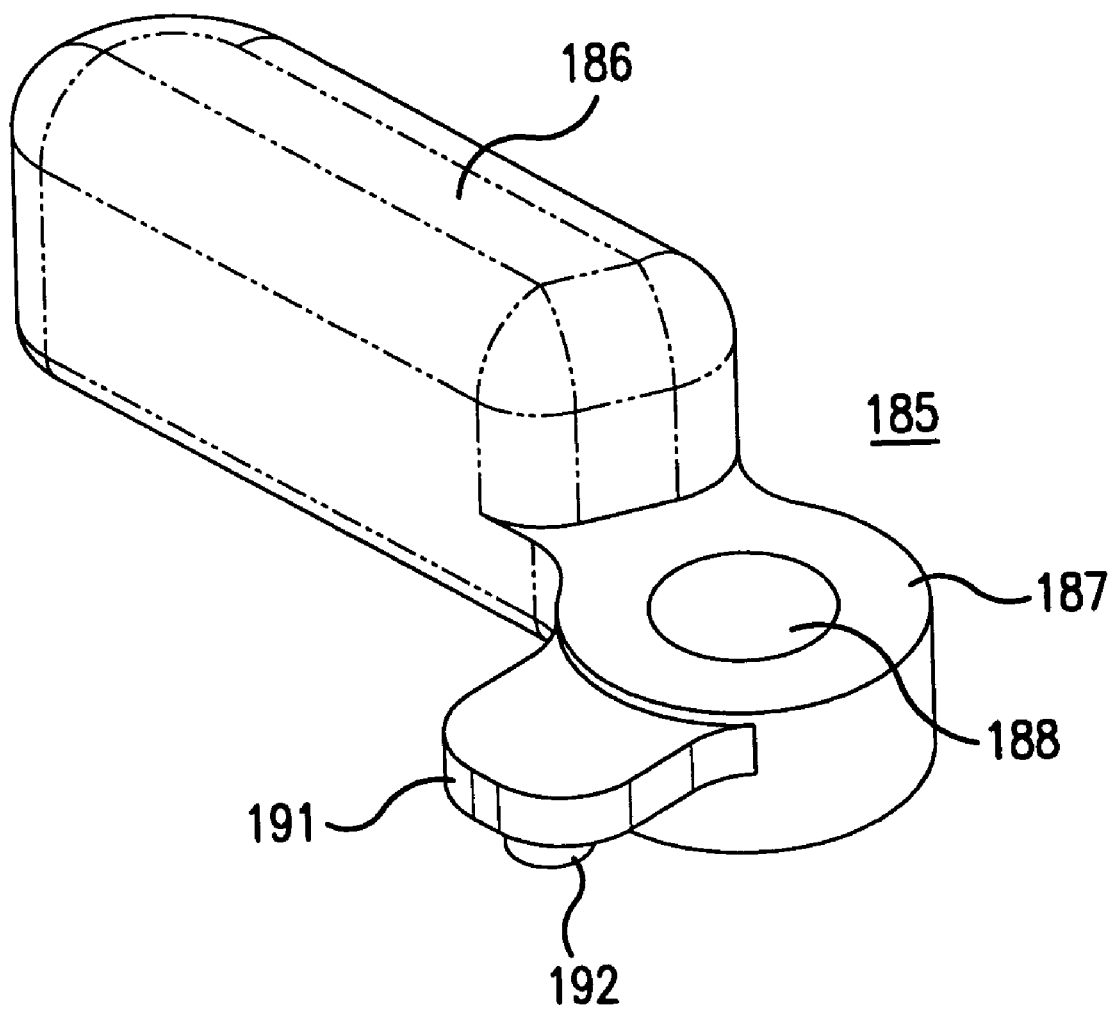
FIG. 21 is a perspective view of a ratchet release button of the handle assembly of the clamp of FIG. 1.

FIG. 21 provides an isolated perspective view of the second ratchet release button 185, which has a handle block 186 with a circular boss 187. A hole 188 is provided in the circular boss 187 through which a shoulder screw 189 can be inserted and threadably coupled to a threaded hole 190 on the inner surface 220 of the handle piece 216. An extension 191 extends at an angle from the boss 187, and carries a pin 192 at its bottom surface. The second ratchet release button 185 can be pivoted with respect to the handle piece 216 about a pivot point defined by the shoulder screw 189 and the hole 188.

Figure 22:
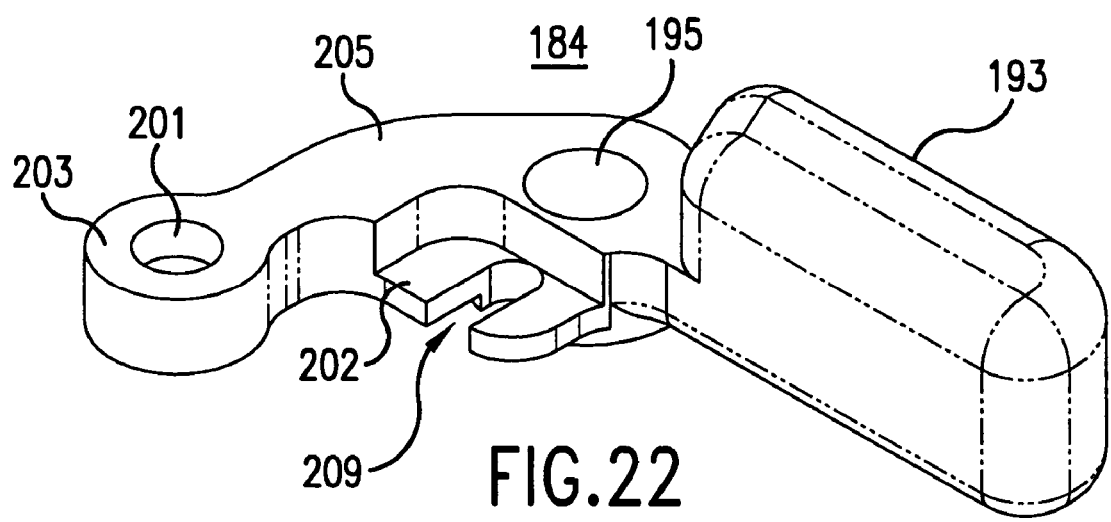
FIG. 22 is a perspective view of another ratchet release button of the handle assembly of the clamp of FIG. 1.

FIG. 22 provides an isolated perspective view of the first ratchet release button 184, which has a handle block 193 with a curved shoulder piece 205 extending at an angle from the handle block 193. A first hole 195 is provided in the shoulder piece 205 adjacent the handle block 193, and is adapted to receive a shoulder screw 197 which can be inserted therethrough and threadably coupled to a threaded hole 199 on the inner surface 220 of the handle piece 216. A circular boss 203 extends from the shoulder piece 205 at an angle from the handle block 193 and the first hole 195, and a second hole 201 is provided in the circular boss 203 through which the boss 183 from the gimble 182 can be inserted. An offset shelf 202 extends from the shoulder piece 205, and has a slot 209 that receives the pin 192 from the second ratchet release button 185. The first ratchet release button 184 can be pivoted with respect to the handle piece 216 about a pivot point defined by the shoulder screw 197 and the hole 195. In addition, the gimble 182 can be pivoted with respect to the first ratchet release button 184 about a pivot point defined by the boss 183 and the hole 201. A screw 211 (see FIG. 26) secures the boss 183 of the gimble 182 to the hole 201.

Figure 23:
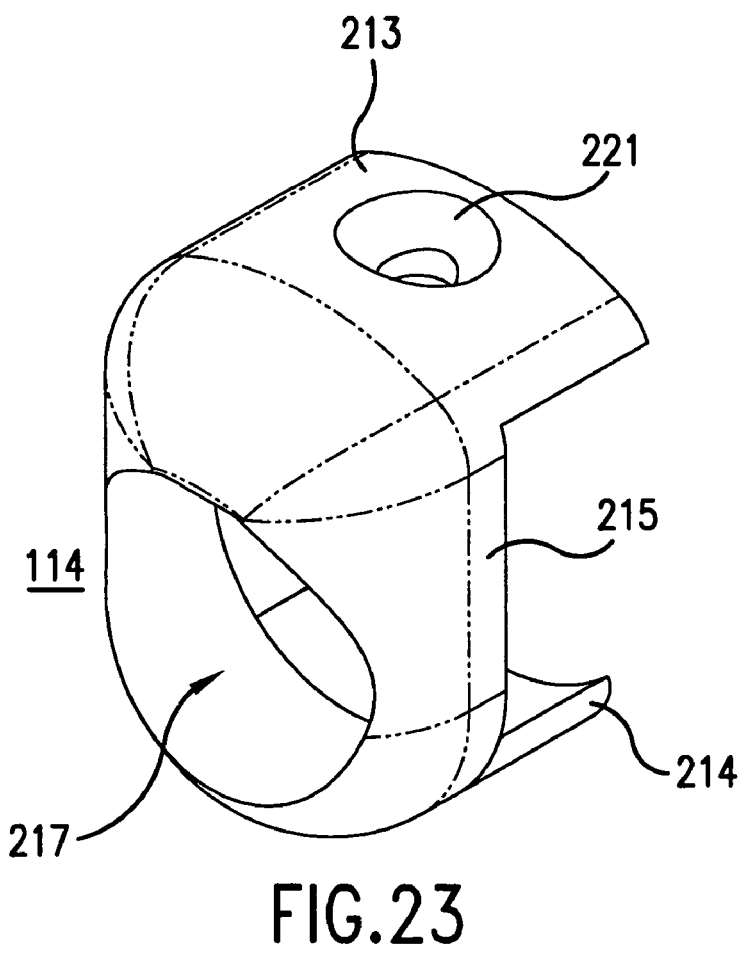
FIG. 23 is a perspective view of a handle end piece of the handle assembly of the clamp of FIG. 1.

FIG. 23 provides an isolated perspective view of a handle end piece 114, which has an upper boss 213 and a lower boss 214 that extend from a cylindrical section 215. The cylindrical section 215 has a bore 217 in which the proximal-most telescoping tube 32a can be retained. The upper boss 213 is attached to the cutaway section 112 of the handle piece 116 by threading a screw 219 (see FIG. 6A) through an opening 221 in the upper boss 213 and a threaded hole 223 in the cutaway section 112 (see FIG. 19). The lower boss 214 is seated over the bottom surface of the handle piece 116. The handle end piece 114 also has a surface 225 that prevents the tube 32a from rotating. This surface 225 can be flat or curved (e.g., concave), or can utilize known pin and slot configurations.

The operation of the ratchet assembly is best illustrated in connection with FIGS. 6A, 15 and 24-26. There are three possible configurations for the ratchet assembly. In all configurations, it should be noted that the spring 167 always biases the tooth 180 of the ratchet 164 in the distal direction towards the ratchet rack 124.

Figure 24:
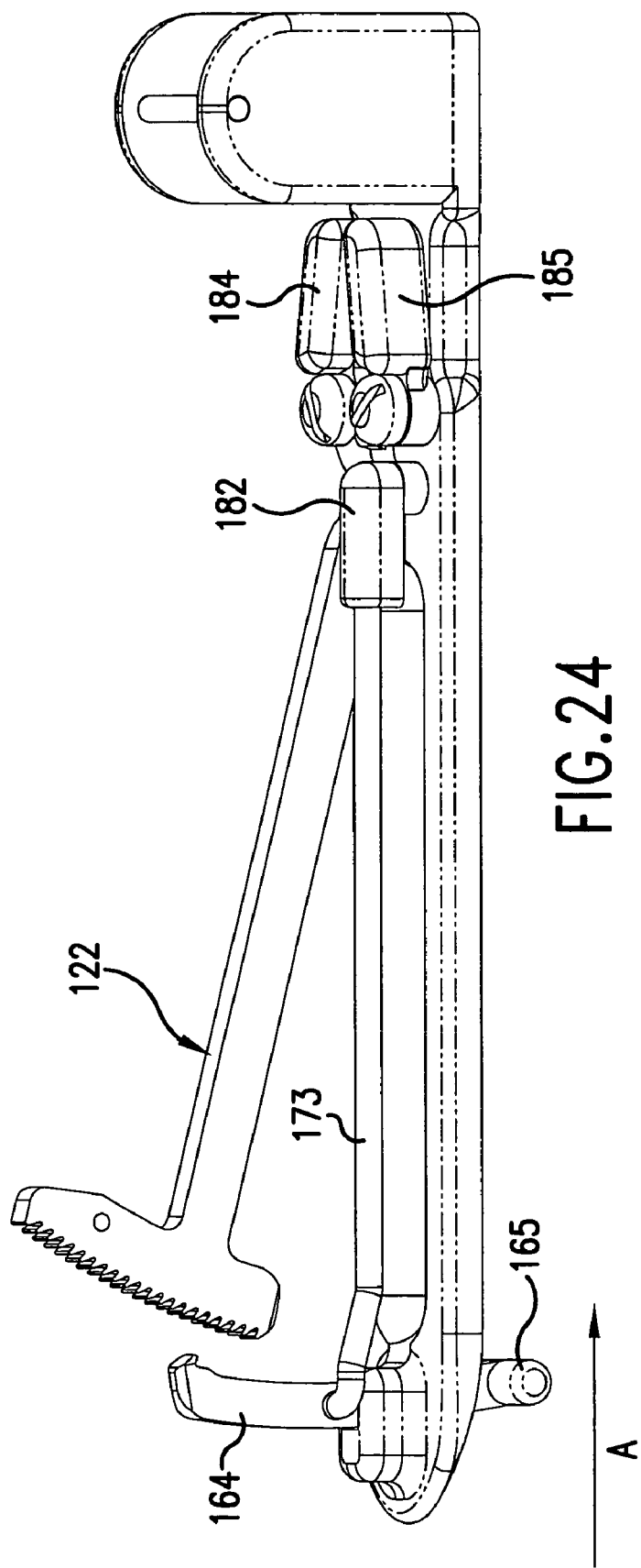
FIG. 24 is side perspective view of portions of the handle assembly of the clamp of FIG. 1 showing the ratchet disengaged from the ratchet rack.

In a first configuration, the teeth 125 and 180 of the ratchet rack 122 and the ratchet 164, respectively, do not engage each other. This is shown in FIG. 24. When in this opened position, the free ends of the handle blocks 193 and 186 of the first and second ratchet release buttons 184 and 185, respectively, are generally pointed at each other at an angle.

In a second configuration, the handle pieces 116, 216 are opened, thus the teeth 125 and 180 of the ratchet rack 122 and the ratchet 164, respectively, do not engage each other, and the tooth 180 on the ratchet 164 extends in a distal direction past the teeth 125 on the ratchet rack 122. This is shown in FIG. 6A. When in this position, the free ends of the handle blocks 193 and 186 of the first and second ratchet release buttons 184 and 185, respectively, exactly parallel to each other because the bias of the spring 167 causes the boss 203 of the first ratchet release button 184 to contact the boss 187 of the second ratchet release button 185.

Figure 25:
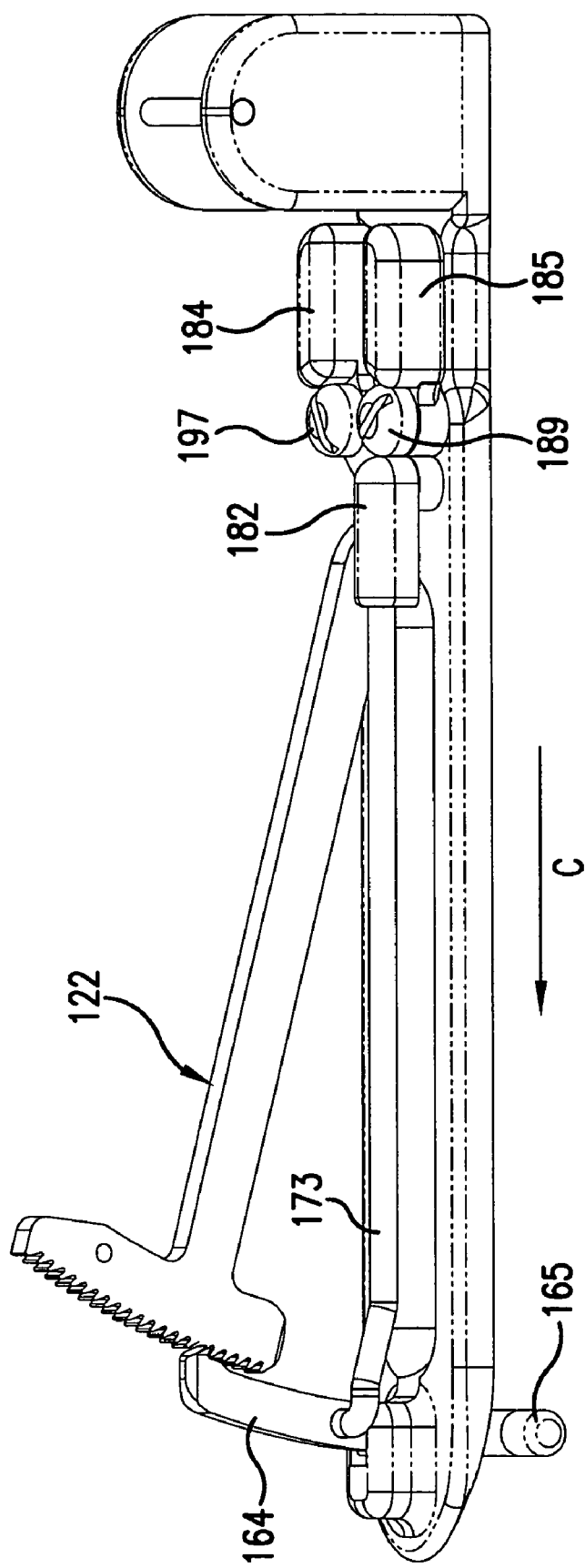
FIG. 25 is a side perspective view of portions of the handle assembly of the clamp of FIG. 1 showing the ratchet engaged to the ratchet rack.
Figure 26:
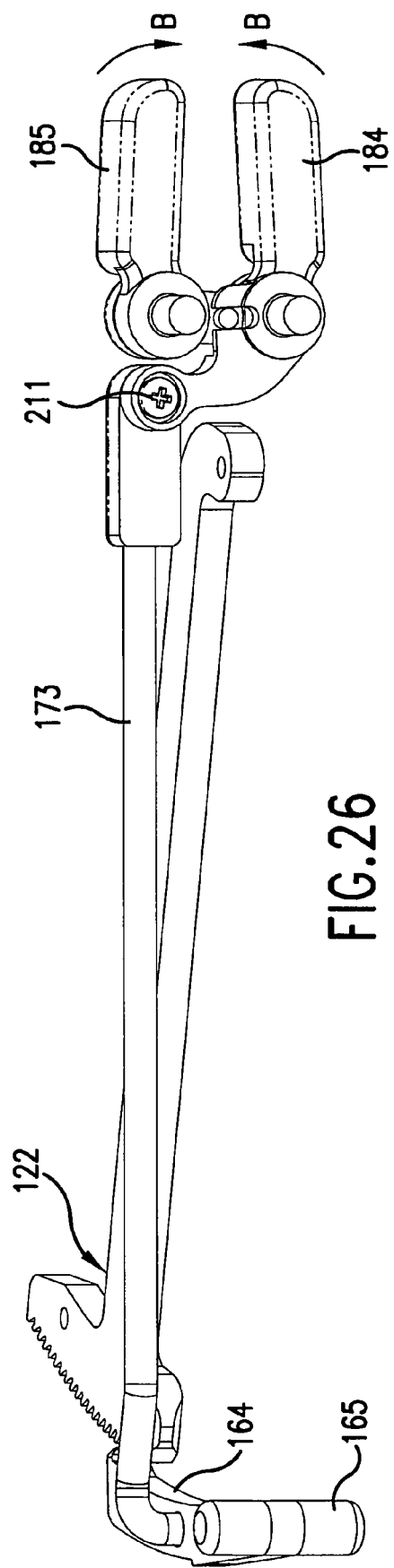
FIG. 26 is a bottom perspective view of portions of the handle assembly of the clamp of FIG. 1 showing the ratchet engaged to the ratchet rack.

In a third configuration, as the tooth 180 pivots in the distal direction (about the pivot point defined by dowel pin 175), the rod 173 and the gimble 182 are pushed in the distal direction to pivot the first ratchet release button 184 about the pivot point defined by the boss 183. The tooth 180 engages a selected tooth 125 on the ratchet rack 122. This is shown in FIGS. 25 and 26. When in this position, the free ends of the handle blocks 193 and 186 of the first and second ratchet release buttons 184 and 185, respectively, are almost, but not exactly, parallel to each other. The surgeon can lock the jaws 260, 262 at varying degrees of clamping force by selecting a different tooth 125 to be engaged with the tooth 180.

The engagement between the tooth 180 and a selected tooth 125 can be released in one or both of two ways. The surgeon can push the handles 165 in the distal direction indicated by the arrow A in FIGS. 6A and 24, thereby pivoting the ratchet 164 about the pivot point 175 so that the tooth 180 is pivoted in a direction opposite to the arrow A, which releases the engagement between the tooth 180 and a selected tooth 125. Thus, the handles 165 operate as levers to pivot the ratchet 164. Alternatively, the surgeon can press one or both of the first and second ratchet release buttons 184 and 185 towards each other in the direction of arrow B in FIG. 26. The inward pivoting motion of one or both of the ratchet release buttons 184, 185 will cause the circular boss 203 and the boss 183 to pivot in the proximal direction, thereby pushing the gimble 182 and the transmission rod 173 in a proximal direction (see arrow C in FIG. 25) to pivot the ratchet 164 about the pivot point 175 so that the tooth 180 is pivoted in a direction opposite to the arrow A, thereby releasing the engagement between the tooth 180 and a selected tooth 125.

The handle assembly 26 is normally biased to the open position that is shown in FIGS. 1 and 6A. As described above, when a user grips the two handle pieces 116 and 216 together, the pivoting at the pivot points defined by the pins 133 and 160 will push the transverse piece 124 in a proximal direction (see arrow C in FIG. 25), which in turn pulls the adjuster piece 130 and the cable housing 128 in the same proximal direction. As the cable housing 128 travels in the proximal direction, it will pull the cable 40 along with it, causing the cable 40 to be pulled in the proximal direction as well.

When the user's grip on the handle pieces 116, 216 is released, the spring 420 in the gripping assembly 30 (described in greater detail below) will bias the jaws 260 and 262 open, which will pull the cable 40 in a distal direction (i.e., opposite to arrow C), and in so doing, will also pull the handle pieces 116, 216 apart (i.e., open).

Locking Assembly for Locking Telescoping Tubes 32

FIGS. 9A-9C and 10 illustrate a locking assembly that is used to lock and secure the distal-most telescoping tube 32*b* to the gripping assembly 30. The locking assembly also includes an alignment mechanism that (1) guides and aligns the jaws of the gripping assembly 30 with the shaft 22 and the telescoping tubes 32, and (2) prevents the jaws 260, 262 of the gripping assembly 30 from rotating when the telescoping tubes 32 extend across the entire shaft 22 and are secured to the gripping assembly 30.

The locking assembly includes (1) a helix cylinder 58 that is secured to the gripping assembly 30, and (2) a lock housing 70 that is movable with respect to the helix cylinder 58 and which can be removably secured to the helix cylinder 58.

Figure 11A:
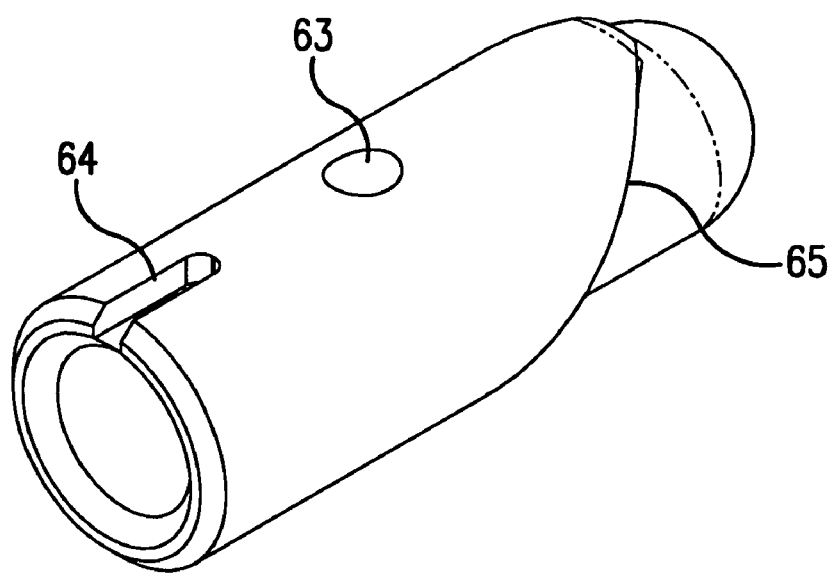
FIGS. 11A, 11B and 11C are top perspective, bottom perspective, and cross-sectional views, respectively, of the helix cylinder of the clamp of FIG. 1.
Figure 11B:
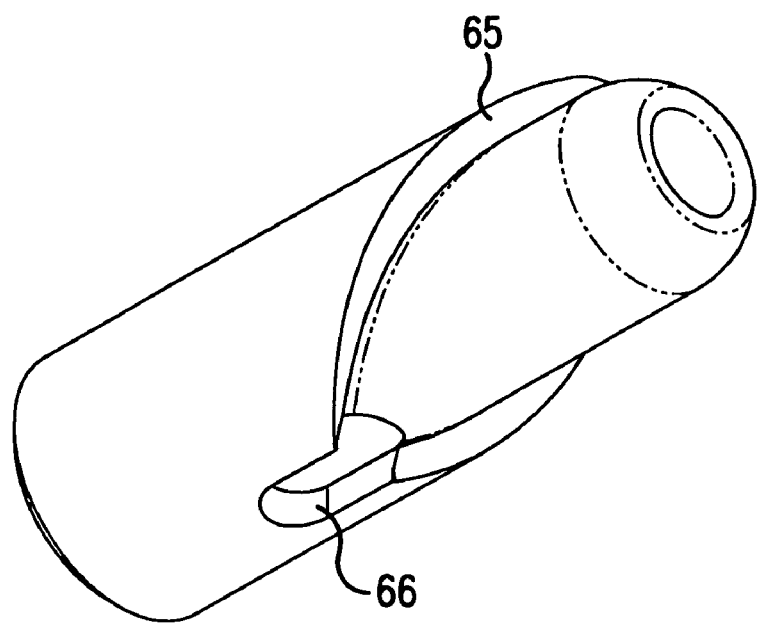
Figure 11C:
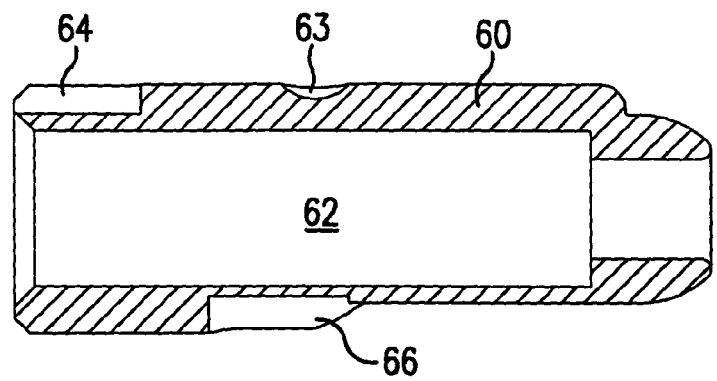

Referring to FIGS. 11A-11C, the helix cylinder 58 has a generally cylindrical body 60 having a bore 62 extending therethrough. A dimple 63 is provided on the outer surface of the body 60 for receiving the ball 87 of the lock housing 70 (as described below). A first longitudinal slot 64 extends from the distal end of the body 60 for a short distance along the body 60, and functions to align the helix cylinder 58 rotationally when the helix cylinder 58 is welded to the gripping assembly 30 (as described below). A helical shoulder 65 is provided along the outer surface of the body 60, extending helically from adjacent the proximal end of the body 60 until it terminates at a second short longitudinal slot 66 at the bottom of the body 60. A spring 420 is retained inside the bore 62 and overlies the cable 40 (which extends through the bore 62), as best shown in FIG. 9A.

Figure 9A:
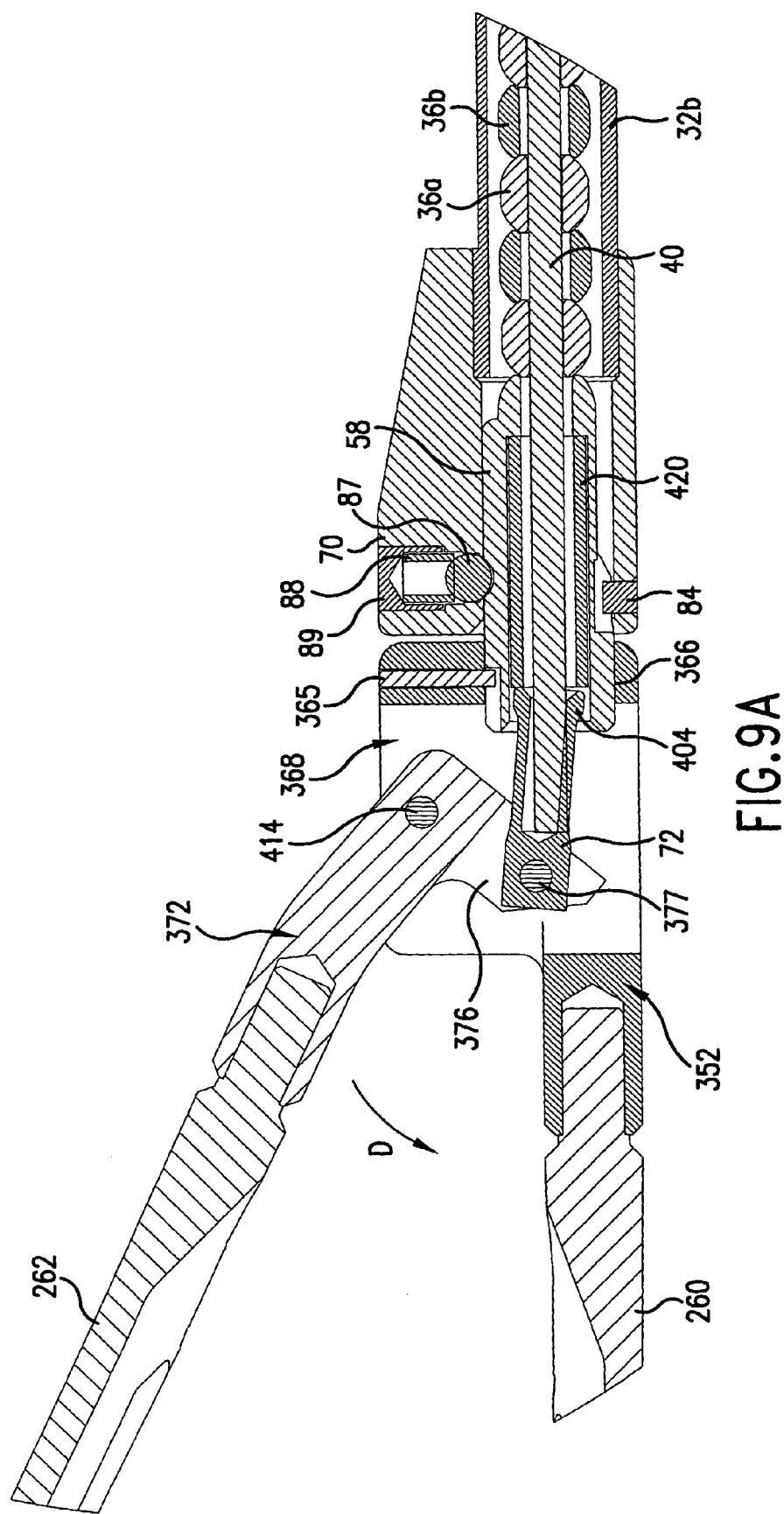
FIG. 9A is a cross-sectional view of the gripping assembly of the clamp of FIG. 1 with the jaws open and the lock mechanism locked with the helix cylinder.
Figure 9B:
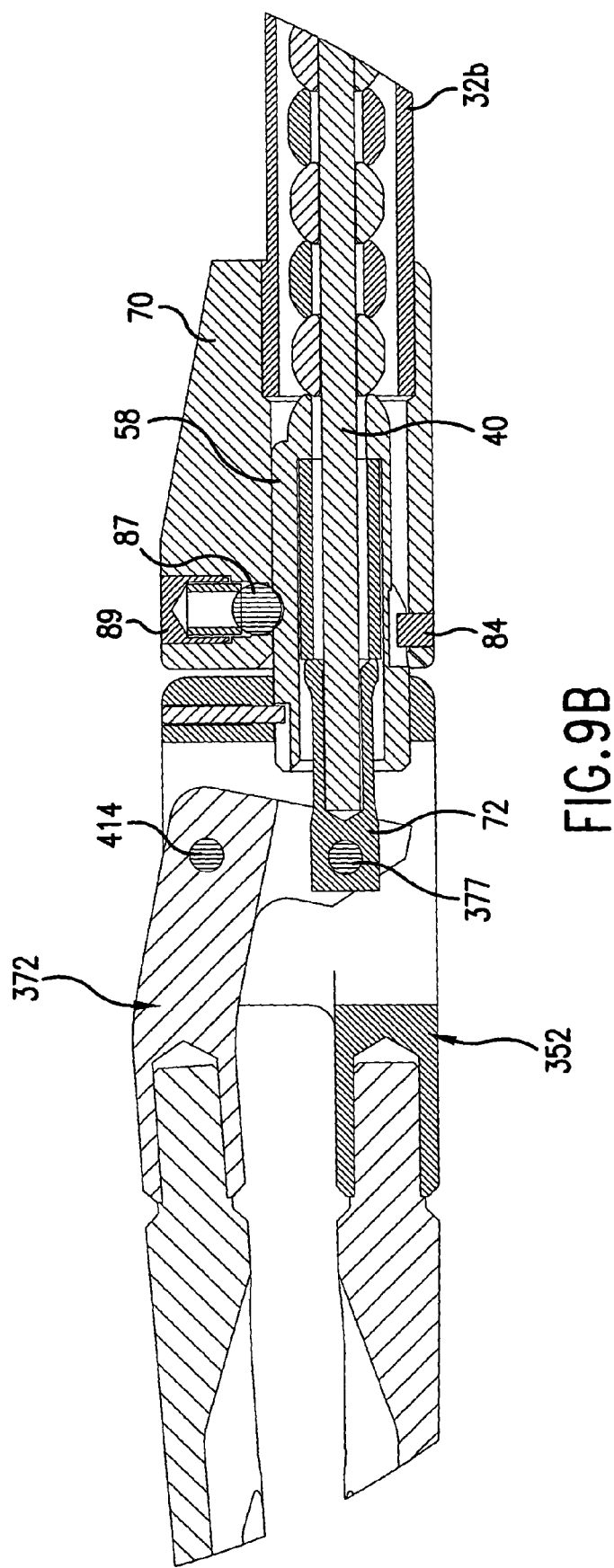
FIG. 9B is a cross-sectional view of the gripping assembly of the clamp of FIG. 1 with the jaws closed and the lock mechanism locked with the helix cylinder.
Figure 9C:
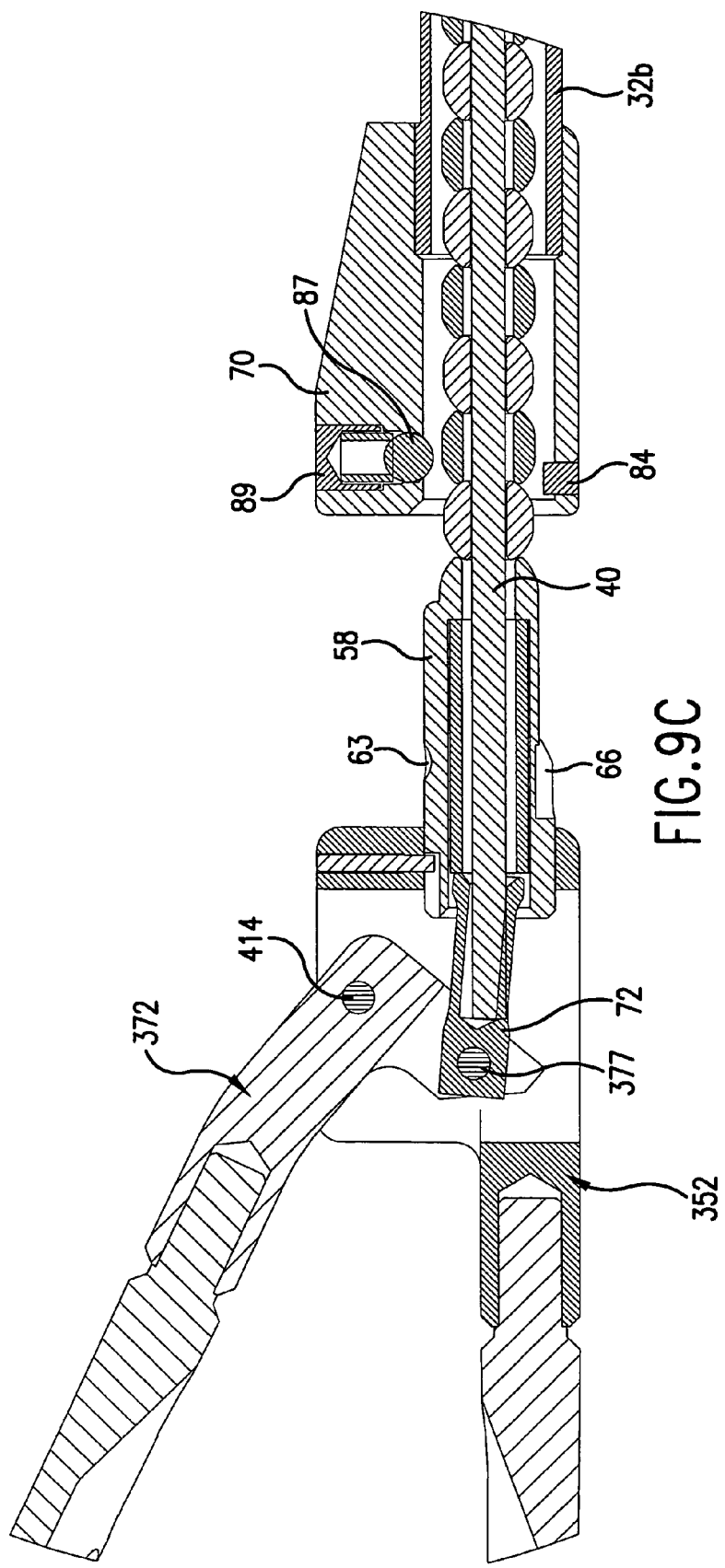
FIG. 9C is a cross-sectional view of the gripping assembly of the clamp of FIG. 1 with the jaws open and the lock mechanism disengaged from the helix cylinder.
Figure 14A:
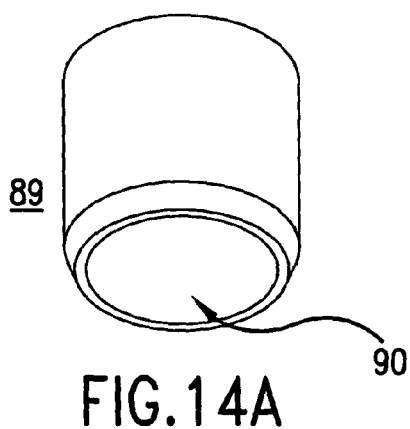
FIGS. 14A and 14B are perspective and cross-sectional views, respectively, of the dowel pin used with the lock mechanism of the clamp of FIG. 1.
Figure 14B:
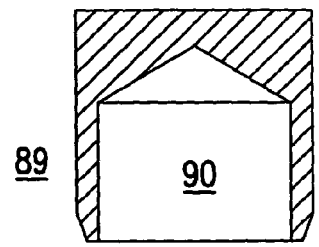

Referring now to FIGS. 2, 9A-9C and 13A-13C, the lock housing 70 is attached to the distal-most telescoping tube 32*b*. The lock housing 70 has a generally rectangular body 77 having a generally cylindrical throughbore that is divided into two sections, a distal section 78 and a proximal section 79 that has a larger diameter than the diameter of the distal section 78. A step 80 defines the transition from the distal section 78 to the proximal section 79. A portion of the distal-most telescoping tube 32*b* is adapted to be retained inside the proximal section 79, and the helix cylinder 58 is retained inside the distal section 78. The step 80 prevents the distal-most telescoping tube 32*b* from extending into the distal section 78. The top outer surface 81 of the lock housing 70 can be angled or slanted to provide a convenient push surface for the user's finger, and ridges 82 can be provided anywhere along the outer surface (e.g., along the outer side walls) of the lock housing 70 for gripping purposes. A bottom hole 83 extends from the outer surface of the body 77 into the distal section 78 of the throughbore, and a dowel pin 84 is received inside the hole 83. A transverse bore 85 extends from the outer surface of the body 77 into the distal section 78 of the throughbore. The transverse bore 85 has a shoulder 86 adjacent its opening into the distal section 78. As shown in FIGS. 9A-9C, a ball 87 is seated in the shoulder 86, and protrudes slightly into the distal section 78. The shoulder 86 prevents the ball 87 from falling into the distal section 78. A spring 88 is placed in the transverse bore 85 and is pressed against the ball 87 to maintain the ball 87 against the shoulder 86. Another dowel pin 89 is positioned over the spring 88 and the ball 87. Referring to FIGS. 14A and 14B, the dowel pin 89 has a interior bore 90 that retains the spring 88, with the spring 88 abutting at one end against the ball 87 and at the other end against the interior wall of the bore 90. The dowel pin 89 can be secured inside the bore 90 by screwing, pressing, brazing, gluing or welding the dowel pin 89 into the bore 90.

The parts of the ball 87 that protrude into the distal section 78 facilitate removable engagement with the dimple 63 of the helix cylinder 58 in the following manner (see FIGS. 9A-9C): when the helix cylinder 58 is inserted into the distal section 78, the body 60 of the helix cylinder 58 forces the ball 87 radially outwardly and compresses the spring 88. As the helix cylinder 58 is continued to be inserted into the distal section 78, the ball 87 will eventually become aligned with the dimple 63, at which time the natural bias of the spring 88 will force the protruding part of the ball 87 into the dimple 63 to lock the lock housing 70 at a defined position with respect to the helix cylinder 58. This combination of an outward radial force (from the body 60 of the helix cylinder 58) and an inward radial force (from the spring 88) locks the lock housing 70 to the helix cylinder 58.

Figure 12A:
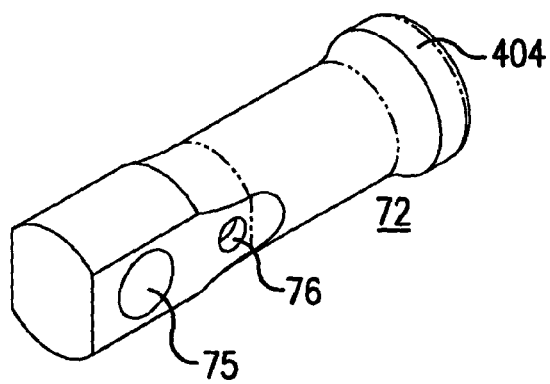
FIGS. 12A and 12B are perspective and cross-sectional views, respectively, of the cable holder in the gripping assembly of the clamp of FIG. 1.
Figure 12B:
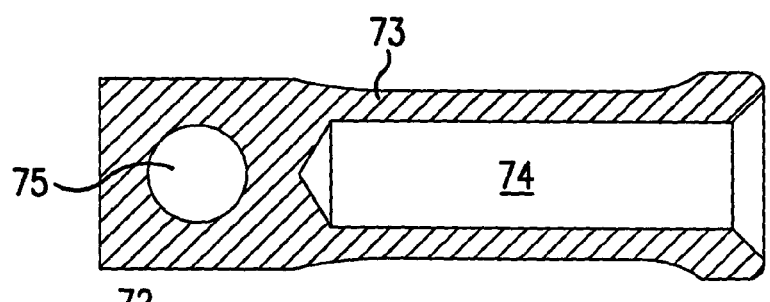
Figure 13A:
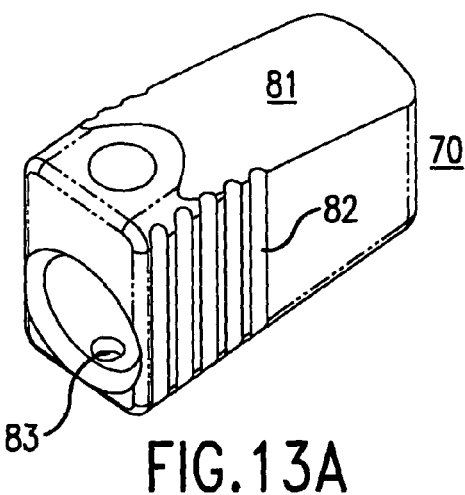
FIGS. 13A and 13B are perspective and cross-sectional views, respectively, of the lock mechanism of the clamp of FIG. 1.
Figure 13B:
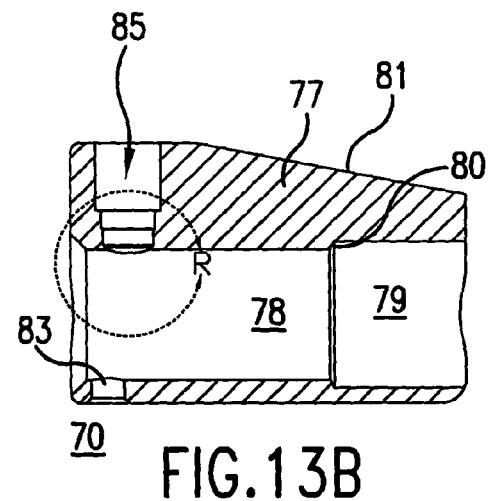
Figure 13C:
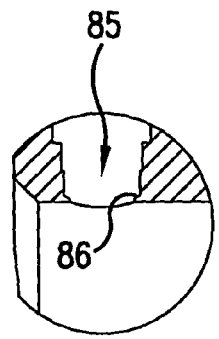
FIG. 13C is an enlarged sectional view of the region labeled R in FIG. 13B.

A portion of a cable holder 72 (that is part of the gripping assembly 30) is retained inside the bore 62 of the helix cylinder 58 and adapted for reciprocating movement in the bore 62. The cable holder 72 retains the distal-most end of the cable 40. Referring now to FIGS. 12A-12B, the cable holder 72 has a generally cylindrical body 73 having a bore 74 extending from its proximal end and terminating at about the center of the body 73. A through-hole 75 is provided adjacent the distal end of the body 73 and is adapted to receive the pin 377 of the gripping assembly 30 (as described below). A vent hole 76 can be provided in the body 73 for manufacturing purposes such as brazing, gluing or welding the cable 40.

As shown in FIGS. 9A-9C and 10, the cable 40 extends from the shaft 22 through the helix cylinder 58 (and the spring 420) and into the bore 74 of the cable holder 72. This distal-most end of the cable 40 is secured inside the bore 74 of the cable holder 72 by brazing, welding, crimping or gluing.

The lock housing 70 and the helix cylinder 58 can function to guide and align the jaws 260, 262 of the gripping assembly 30 with the shaft 22 and the telescoping tubes 32, and to prevent the jaws 260, 262 of the gripping assembly 30 from rotating when the telescoping tubes 32 extend across the entire shaft 22 and are secured to the gripping assembly 30. Referring first to FIGS. 2 and 9C, the lock housing 70 is shown as being disengaged from the helix cylinder 58, so that the lock housing 70 can be retracted together with the telescoping tube 32*b* that is attached to it. The lock housing 70 can be retracted proximally until it is adjacent the handle end piece 114. When it is desired to completely cover the shaft 22 with the telescoping tubes 32, the user can grip the lock housing 70 and then pull it towards the helix cylinder 58. As the lock housing 70 approaches and engages the helix cylinder 58, two events occur. First, the dowel pin 84 will contact the helical shoulder 65, and be guided by the helical shoulder 65 until the dowel pin 84 is seated inside the second slot 66, as shown in FIGS. 1 and 9A. Second, the helix cylinder 58 is inserted into the distal section 78 of the lock housing 70 until the ball 87 becomes aligned with the dimple 63, at which time the natural bias of the spring 88 will force the protruding part of the ball 87 into the dimple 63. Once both of these events have occurred, the lock housing 70 is locked at a defined position with respect to the helix cylinder 58 in a manner such that one cannot rotate with respect to the other. As a result, rotation of the jaws 260, 262 of the gripping assembly 30 can be prevented when the lock housing 70 is locked with the helix cylinder 58.

The Gripping Assembly 30

One embodiment of the gripping assembly 30 is illustrated in connection with FIGS. 9A-9C and 10. The gripping assembly 30 is used to grip tissue or other anatomical structures (such as but not limited to a blood vessel) during a surgical procedure. The gripping assembly 30 has a pair of gripping jaws 260 and 262 that can be pivoted to open and close with respect to each other. Each jaw 260 and 262 has an insert (not shown) provided thereon. These inserts can be embodied in the form of any of the known inserts that are currently commercially available. The techniques and mechanisms for securing the inserts to the jaws 260 and 262 are also well-known and will not be described herein.

The proximal end 266 of the first jaw 260 is secured inside a bore 350 of a stationary jaw base 352. The jaw base 352 has a distal tubular section 354 that defines the bore 350, a holder section that has a pair of opposing vertical walls 356 and 358, and a proximal wall section 360 that is attached to the helix cylinder 58. The opposing vertical walls 356 and 358 define a space 368 therebetween, and each vertical wall 356 and 358 has an aligned opening 362 and 364, respectively. The proximal wall section 360 has a bore 366 through which a portion of the helix cylinder 58 (and the cable 40 carried therein) can extend. A hole 363 extends from the top surface of the proximal wall section 360 into the bore 366, and a dowel pin 365 is inserted through the hole 363 and into the slot 64 of the helix cylinder 58 to secure a portion of the helix cylinder 58 in a non-rotatable and fixed position inside the proximal wall section 360. According to one embodiment, the helix cylinder 58 can be welded to the proximal wall section 360. Alternatively, the helix cylinder 58 can also be pressed, glazed, glued or screwed into the jaw base 352.

The proximal end 300 of the second jaw 262 is secured inside a bore 370 of a pivoting jaw base 372. The jaw base 372 has an L-shaped configuration, with a longitudinal portion 374 that defines the bore 370, and a transverse portion 376 that has a hole 378. The transverse portion 376 is comprised of two parallel walls that define a space therebetween, and with aligned second holes 380 provided in each parallel wall.

The cable holder 72 carries the distal end of the cable 40 and extends through the bore 366 of the jaw base 352 and into the space 368. The two parallel walls of the transverse portion 376 of the jaw base 372 also extend into the space 368. The through-hole 75 of the cable holder 72 is received in the space between the two parallel walls of the transverse portion 376, and is aligned with the openings 380 on each of these parallel walls. A pin 377 extends through the through-hole 75 and the openings 380 to create a pivoting connection between the cable holder 72 and the jaw base 372. In addition, the openings 362 and 364 in the jaw base 352 are aligned with the hole 378 of the jaw base 372, so a dowel pin 414 can extend through the openings 362, 364 and the hole 378 to create a pivoting connection between the two jaw bases 352 and 372.

As described above, the spring 420 is provided inside the helix cylinder 58, and functions to continuously bias the jaw base 372 with respect to the jaw base 352 by pushing or exerting a bias against the proximal end 404 of the cable holder 72. In particular, the bias that is exerted against the proximal end 404 of the cable holder 72 pushes the cable holder 72 in the distal direction against the pin 377 to pivot the jaw base 372 about the pin 414 in a clockwise direction opposite to the arrow D as viewed in FIG. 9A, thereby pivoting the jaw base 372 away from the jaw base 352 to open the jaws 260, 262. At the same time, movement by the cable holder 72 in the distal direction will pull the cable 40 in a distal direction, which will pull the cable holder 128, the adjuster piece 130, the pin 160, and the transverse piece 124 in the distal direction. By pulling the transverse piece 124 in the distal direction, the ratchet rack 122 pivots about the pin 133 to push the handle pieces 116 and 216 apart from each other.

To close the jaws 260, 262, the surgeon grips the handle pieces 116, 216 towards each other to overcome the bias of the spring 420. In particular, when the surgeon grips the handle pieces 116, 216, the ratchet rack 122 is pivoted about the pin 133, and the transverse piece 124 is pivoted about the pin 160, to pull the transverse piece 124 in the proximal direction. This will pull the cable holder 128 and the adjuster piece 130 in the proximal direction, so that the cable 40 carried in the cable holder 128 is also pulled in the proximal direction. When the cable 40 is pulled in the proximal direction, the distal end of the cable 40 that is secured to the cable holder 72 will also pull the cable holder 72 in the proximal direction. As the cable holder 72 moves in the proximal direction, the cable holder 72 will overcome the bias of the spring 420 (see FIG. 9B), and will rotate the transverse portion 376 of the jaw base 372 in the direction of arrow D shown in FIG. 9A about the axis defined by the pin 414. This causes the pivoting jaw base 372 to pivot towards the stationary jaw base 352 to close the jaws 260, 262 so as to grip a blood vessel, tissue or other anatomical structure.

When the jaws 260, 262 have been closed, the surgeon can retract the telescoping tubes 32 completely to nest and store all the telescoping tubes 32 inside the handle assembly 26, or the surgeon can retract some, but not all, of the telescoping tubes 32 so that only a portion (but not the entire length of) the shaft 22 is exposed. The exposed portions of the shaft 22 will then be bendable by the surgeon in any direction desired by the surgeon, so that the handle assembly 26 can be moved away from the surgical site and not impede the surgeon's access to the surgical site.

Figure 29:
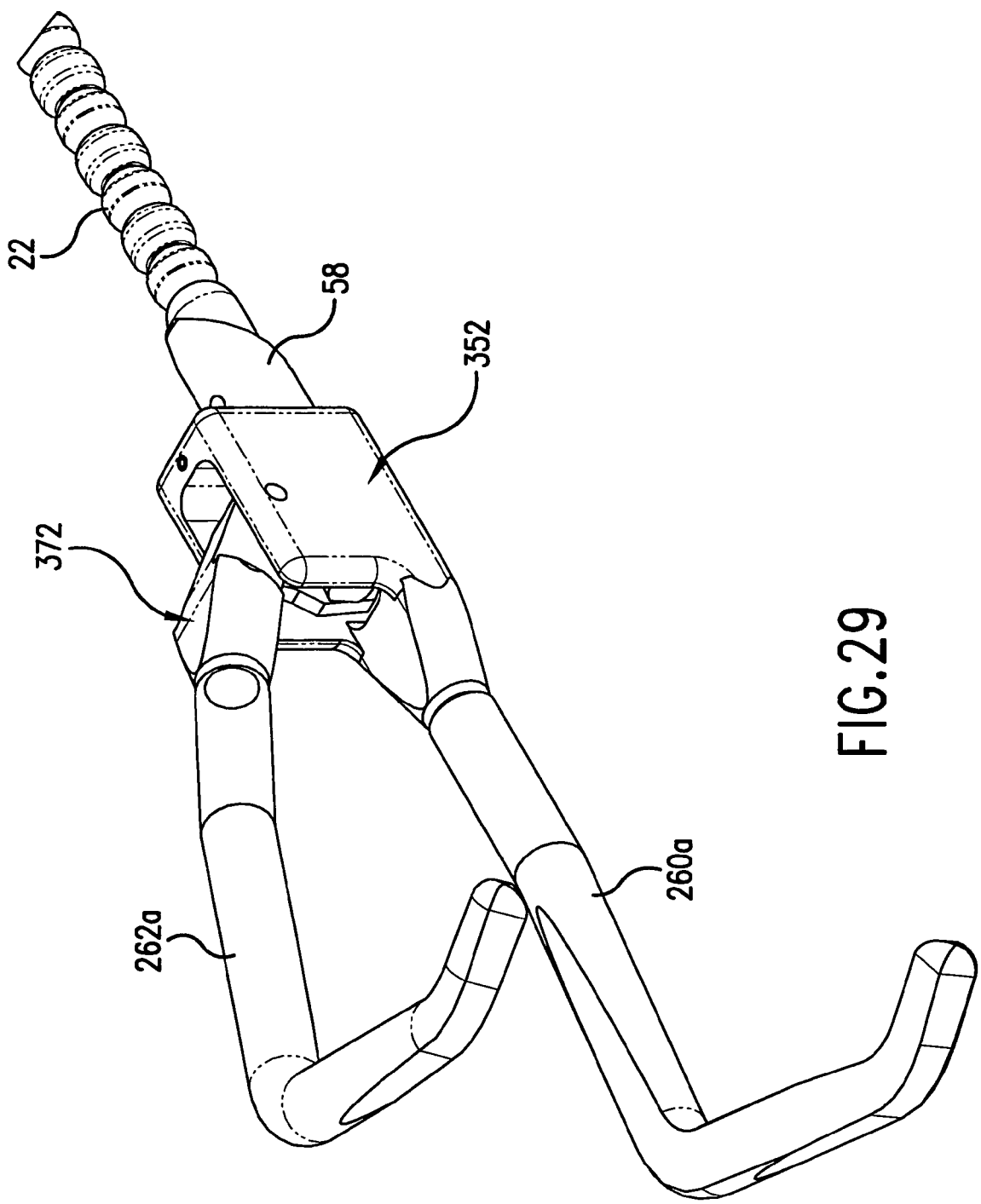
FIG. 29 is a perspective view of the gripping assembly of the clamp of FIG. 1 shown in use with different jaws.

The jaws 260, 262 can be removed from the bores 350 and 370, respectively, and replaced with a different set of jaws, such as 260a, 262a that are shown in FIG. 29. Reference should be made to U.S. Pat. No. 6,293,954 that is also assigned to the present assignee, which describes how removable jaws such as 260a, 262a can be implemented. The entire disclosure of U.S. Pat. No. 6,293,954 is hereby incorporated by this reference as though set forth fully herein.

Thus, the present invention provides a clamping device (the clamp assembly 20) that can effectively clamp a blood vessel, tissue or other anatomical structure at a surgical site, while not interfering with the surgeon's access to the surgical site. The shaft assembly that includes a flexible shaft and nested telescoping tubes 32 allows the shaft assembly to be both completely rigid and completely flexible. The rigid shaft that is formed when the telescoping tubes 32 are fully deployed is capable of withstanding axial loads, side loads, moments and torques applied to the jaws 260, 262. As a result, the surgeon can use the jaws 260, 262 to poke and prod around the surgical site. In addition, the lock housing 70 ensures that the jaws 260, 262 are not rotatable with respect to the shaft 22.

EXAMPLE

The clamp 20 of the present invention is especially well-suited for use in minimally-invasive procedures where the jaws 260, 262 can be introduced through a port, trocar or small incision (hereinafter collectively referred to as "Port"). Such minimally-invasive procedures can include applications such as endoscopic or laproscopic applications. For example, during a minimally-invasive procedure, a surgeon may need to use an endoscope to view the surgical activity at the site of the procedure. In such minimally-invasive procedures, the Port is of a small size such that the surgeon's hands cannot readily access the surgical site through the Port. As a result, the surgeon can only manipulate the jaws 260, 262 via the handle assembly 26.

When used in a minimally-invasive procedure, the surgeon grips the handle pieces 116, 216 to close the jaws 260, 262, and then introduces the closed jaws 260, 262 and a portion of the shaft 22 through the Port into the interior of a patient. The surgeon then manipulates the jaws 260, 262 (via gripping of the handle pieces 116, 216) to manipulate the blood vessels, tissues and other anatomical structures. During this manipulation, the jaws 260, 262 can be either opened or closed. If closed, the jaws 260, 262 can be used in a similar manner as a retractor or other blunt instrument. If opened, the jaws 260, 262 can be used as a gripping element (i.e., like a clamp) or as a needle holder. The rigidity of the telescoping tubes 32 allows the surgeon to be able to manipulate the jaws 260, 262 solely by controlling the handle pieces 116, 216 that are positioned outside the patient's body. The rigid shaft that is formed by the fully deployed telescoping tubes 32 protrudes through the Port which acts as a fulcrum. For example, if the surgeon wishes to move the jaws 260, 262 to the right, the surgeon merely moves the handle pieces 116, 216 to the left to pivot the shaft 22 about the fulcrum. Next, the surgeon can (if desired) close the jaws 260, 262 by gripping the handle pieces 116, 216 to cause the jaws 260, 262 to grip a vessel, tissue or anatomical structure.

With the shaft 22 extending through the Port, the surgeon can then withdraw the telescoping tubes 32 so that a portion of the shaft 22 is now completely flexible and bendable. The tubes 32 can be withdrawn by first gripping and withdrawing the proximal-most tube 32a which would likely be outside the patient's body. Since the tubes 32 are locked to each other in the manner shown in FIG. 28, withdrawal of the proximal-most tube 32a will cause the tube 32 that is distal to (i.e., adjacent to) the proximal-most tube 32a to be withdrawn slightly as well. At this time, each tube 32 will be pulled proximally, and this pulling force will cause the ball 87 in the lock housing 70 to be disengaged from the dimple 63 of the helix cylinder 58. The surgeon can then grip and withdraw the tube 32 that is distal to (i.e., adjacent to) the proximal-most tube 32a. In this manner, the surgeon can grip and withdraw each tube 32, one at a time, until all distal-most tube 32b has been withdrawn as well. The handle assembly 26 can then be moved away from the surgical site.

Depending on the surgical procedure, some of the telescoping tubes 32 can be extended again (or only some, but not all, of the tubes 32 can be withdrawn) to cover a portion of the shaft 22 to render that portion of the shaft 22 completely rigid again.

In addition, if it is necessary to perform manipulation of other vessels, tissues or anatomical structures at the surgical site, the surgeon can completely extend all the telescoping tubes 32 to render the shaft completely rigid again, and then manipulate the jaws 260, 262 (via the handle pieces 116, 216) according to the steps described above. To extend one or more tubes 32, the surgeon locks each tube 32 to an adjacent tube 32 using the dimples 139 and the tabs 141 according to the technique described above in connection with FIG. 28, and then pushes each tube 32 (starting with the distal-most tube 32b) back through the Port into the patient's body.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A clamp, comprising:
   a handle assembly;
   a gripping assembly having a pair of jaws that can be opened and closed to grip an element;
   a shaft assembly having:
      a flexible shaft having a proximal end that is coupled to the handle assembly and a distal end that is coupled to the gripping assembly, the flexible shaft defining a bore and comprising a plurality of alternating first beads and second beads, each of the first and second beads having a surface;
      wherein each of the second beads has a larger inner diameter than each of the first beads, each of the second beads is supported on the surface of the two adjacent beads at a line of contact, and each of the second beads has a convex shape at the line of contact; and
      a cable which extends through the bore of the flexible shaft, the cable having a proximal end that is operatively coupled to the handle assembly and a distal end that is operatively coupled to the gripping assembly; and,
   a rigid element that can be placed at a first position where the rigid element supports the shaft in a manner where the shaft cannot be bent, and in a second position where the shaft can be bent.

2. The clamp of claim 1, wherein the surface of each of the first beads has a convex shape at the line of contact.

3. The clamp of claim 1, wherein each of the second beads has a larger outer diameter than each of the first beads.

4. The clamp of claim 1, wherein each of the second beads has a smaller outer diameter than each of the first beads.

5. The clamp of claim 1, wherein each of the second beads has the same outer diameter as each of the first beads.

6. The clamp of claim 1, wherein the line of contact is a circular line of contact.

* * * * *